United States Patent
Janna et al.

(10) Patent No.: US 12,251,164 B2
(45) Date of Patent: Mar. 18, 2025

(54) METHODS AND SYSTEM FOR MANUFACTURING A JOINT IMPLANT

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Sied W. Janna, Memphis, TN (US); John Rose, Collierville, TN (US); Darren J. Wilson, Hull (GB); Helen K. Brantley, Germantown, TN (US)

(73) Assignees: SMITH & NEPHEW, INC., Memphis, TN (US); SMITH & NEPHEW ORTHOPAEDICS AG SMITH, Zug (CH); NEPHEW ASIA PACIFIC PTE. LIMITED, Singapore (SG)

( * ) Notice: Subject to any disclaimer, the term of this patent is extended or adjusted under 35 U.S.C. 154(b) by 725 days.

(21) Appl. No.: 17/601,514

(22) PCT Filed: Apr. 3, 2020

(86) PCT No.: PCT/US2020/026530
§ 371 (c)(1),
(2) Date: Oct. 5, 2021

(87) PCT Pub. No.: WO2020/206216
PCT Pub. Date: Oct. 8, 2020

(65) Prior Publication Data
US 2022/0142710 A1  May 12, 2022

Related U.S. Application Data

(60) Provisional application No. 62/901,404, filed on Sep. 17, 2019, provisional application No. 62/875,888, (Continued)

(51) Int. Cl.
*A61B 34/00* (2016.01)
*A61B 34/10* (2016.01)
(Continued)

(52) U.S. Cl.
CPC .............. *A61B 34/10* (2016.02); *A61B 34/20* (2016.02); *A61B 34/30* (2016.02); *G06N 3/045* (2023.01);
(Continued)

(58) Field of Classification Search
CPC ......... A61B 34/10; A61B 34/20; A61B 34/30; A61B 34/76; A61B 2034/105;
(Continued)

(56) References Cited

U.S. PATENT DOCUMENTS 8,078,440 B2   12/2011   Otto et al.
8,883,915 B2   11/2014   Myung et al.
(Continued)

FOREIGN PATENT DOCUMENTS

EP   2338530 A2 *   6/2011   ......... A61F 2/30756

OTHER PUBLICATIONS

International Search Report and Written Opinion for International application No. PCT/US2020/026530, mailed on Jul. 1, 2020, 13 pages.

*Primary Examiner* — Khai M Nguyen
(74) *Attorney, Agent, or Firm* — KDW Firm PLLC

(57) ABSTRACT

Methods and systems for treating osteochondral defects (OCDs) are disclosed. The methods include collecting surface data of a joint using image-free methods, generating a three-dimensional (3D) healthy bone model based on the surface data and a database of healthy bone anatomies, defining a boundary of the OCD on the joint, and generating a 3D implant model based on the 3D healthy bone model and the boundary. The method may also include manufacturing
(Continued)

an implant based on the 3D implant model, generating an implantation plan, resecting the joint according to the implantation plan, and placing the implant into the resected cavity. The 3D implant model may include a first and second porous layer separated by a nonporous layer. A polymer material is overmolded onto the second porous layer and treated to exhibit properties that mimic cartilage, while the first porous layer allows the implant to fuse to patient bone.

20 Claims, 20 Drawing Sheets

Related U.S. Application Data filed on Jul. 18, 2019, provisional application No. 62/830,078, filed on Apr. 5, 2019.

(51) Int. Cl.
| | |
|---|---|
| *A61B 34/20* | (2016.01) |
| *A61B 34/30* | (2016.01) |
| *G06N 3/045* | (2023.01) |
| *G06N 3/08* | (2023.01) |
| *G16H 20/40* | (2018.01) |
| *G16H 40/63* | (2018.01) |
| *G16H 50/50* | (2018.01) |
| *A61B 17/00* | (2006.01) |
| *A61B 90/00* | (2016.01) |
| *A61B 90/50* | (2016.01) |
| *G06N 5/046* | (2023.01) |

(52) U.S. Cl.
CPC ............... *G06N 3/08* (2013.01); *G16H 20/40* (2018.01); *G16H 40/63* (2018.01); *G16H 50/50* (2018.01); *A61B 2017/00973* (2013.01); *A61B 2034/105* (2016.02); *A61B 2034/108* (2016.02); *A61B 2034/2055* (2016.02); *A61B 2034/2068* (2016.02); *A61B 2034/252* (2016.02); *A61B 2034/256* (2016.02); *A61B 2034/258* (2016.02); *A61B 34/76* (2016.02); *A61B 90/03* (2016.02); *A61B 2090/365* (2016.02); *A61B 2090/372* (2016.02); *A61B 2090/502* (2016.02); *G06N 5/046* (2013.01)

(58) Field of Classification Search
CPC ...... A61B 2034/108; A61B 2034/2055; A61B 2034/2068; A61B 2034/252; A61B 2034/256; A61B 2034/258; A61B 90/03; A61B 2090/365; A61B 2090/372; A61B 2090/502; A61B 2017/00973; G16H 20/40; G16H 50/50; G16H 40/63; G06N 3/045; G06N 3/08; G06N 5/046
See application file for complete search history.

(56) References Cited

U.S. PATENT DOCUMENTS

| | | | |
|---|---|---|---|
| 10,342,636 | B2 | 7/2019 | Nowatschin et al. |
| 10,426,571 | B2 | 10/2019 | Krinninger et al. |
| 10,993,777 | B2 | 5/2021 | Nowatschin et al. |
| 2004/0236424 | A1* | 11/2004 | Berez .................. A61B 17/158 623/908 |
| 2005/0267584 | A1 | 12/2005 | Burdulis, Jr. et al. |
| 2008/0306490 | A1* | 12/2008 | Lakin .................... A61B 90/36 606/130 |
| 2010/0256504 | A1* | 10/2010 | Moreau-Gaudry .... A61B 34/20 703/11 |
| 2016/0038291 | A1* | 2/2016 | Netravali ............ A61F 2/30942 606/86 R |
| 2018/0007105 | A1 | 1/2018 | Swenson et al. |
| 2020/0030109 | A1* | 1/2020 | Eltorai ................ A61F 2/30771 |

\* cited by examiner

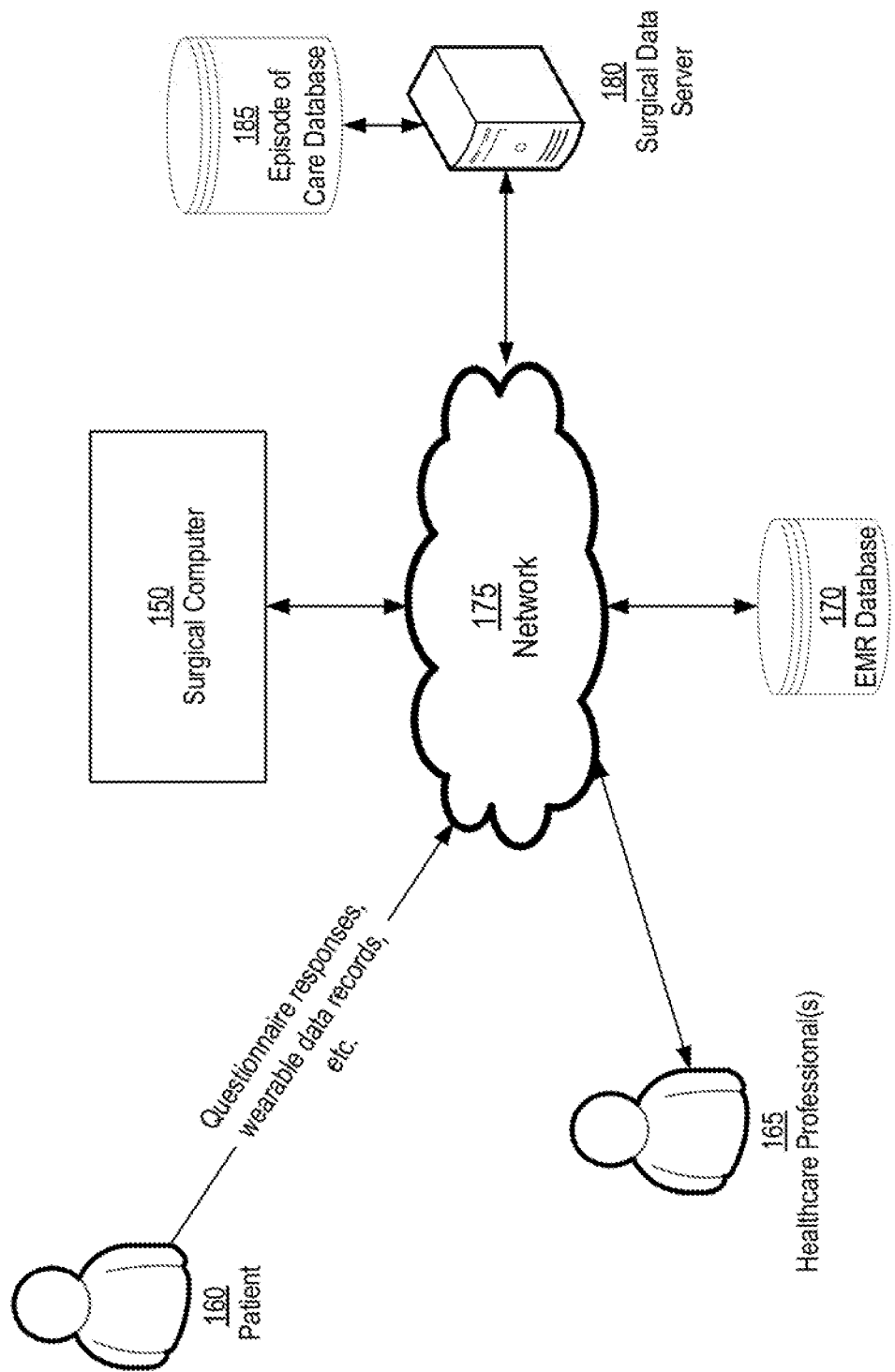

METHODS AND SYSTEM FOR MANUFACTURING A JOINT IMPLANT

CLAIM OF PRIORITY

This application is a U.S. National Stage filing under 35 U.S.C. § 371 of International PCT Application No. PCT/US2020/026530, filed Apr. 3, 2020, which claims the benefit of priority to U.S. Provisional Application No. 62/830,078, titled "Cartilage Repair Device, System and Method," filed Apr. 5, 2019, U.S. Provisional Application No. 62/875,888, titled "Methods and System for Manufacturing a Joint Implant," filed Jul. 18, 2019, and U.S. Provisional Application No. 62/901,404, titled "Cartilage Repair Device, System and Method," filed Sep. 17, 2019, each of which is incorporated herein by reference in its entirety.

TECHNICAL FIELD

The present disclosure relates generally to methods, systems, and apparatuses related to a computer-assisted surgical system that includes various hardware and software components that work together to enhance surgical workflows. More particularly, the present disclosure relates to medical devices for the treatment and repair of osteochondral defects and to methods, devices, and systems for designing, fabricating, and implanting such medical devices. The disclosed techniques may be applied to, for example, shoulder, hip, and knee surgical procedures, as well as other surgical interventions such as arthroscopic procedures, spinal procedures, maxillofacial procedures, rotator cuff procedures, ligament repair and replacement procedures.

BACKGROUND

Articular cartilage is the smooth tissue that covers the ends of bones where they abut to form joints and allows the ends of bones to glide in proximity to each other with little friction when the joint is in motion. Damage to articular cartilage, sometimes referred to as articular lesions, can be caused by trauma, disease (e.g., osteoarthritic degradation), or age. The body does not readily repair damaged cartilage because cartilage does not have direct access to the body's blood supply to surround damaged tissue and provide factors promoting regeneration. Articular lesions can result in further damage to the sub-chondral bone if not treated. Such damage is commonly referred to as an osteochondral defect (OCD). In weight-bearing joints (i.e., the ankles, knees, and hips), OCDs may be associated with pain, loss of function, and long-term complications, such as osteoarthritis. Articular lesions and OCDs can vary widely in size, location, and the degree of damage they may cause. As a result, a treatment plan for a patient with an articular lesion or OCD must be customized to the patient and requires a thorough assessment of the articular lesion or OCD for a number of factors, including the location and size of the articular lesion or OCD and the age and activity level of the patient.

In most cases, surgical treatment, for example arthroscopic surgery, of an articular lesion or OCD is necessary to provide relief for the patient from pain and other symptoms. Arthroscopic surgery options include, for example, debridement, microfracture, abrasion arthroplasty, osteochondral autograft transplantation (OATS, also known as mosaicplasty), and autologous chondrocyte implantation (ACI).

Synthetic implants that replace the damaged cartilage and sub-chondral bone are also used for the treatment of OCDs. These implant devices used to treat OCDs vary in size and material depending on the location of the OCD on the articular joint. Commercially available implants include the Arthrosurface HemiCAP, the BioPoly RS system, and the Episurf Episealer. These implants can range from cobalt chrome plugs anchored into the bone to porous scaffolds seeded with cells to induce chondrification. However, biointegration of synthetic implants into the patient's native joint can be challenging and may vary by patient. Existing synthetic implants typically have pre-defined shapes and sizes, requiring the removal of healthy tissue to conform to the implant during installation. Synthetic implants may also result in incongruence with the surrounding articular surface. Further, damage to the sub-chondral bone in an OCD may destroy the original contours of the bone and make restoring the normal pressures of the knee more difficult. In addition, some implants are made of metal and are nonporous. Such implants may cause damage to cartilage opposing the implants. Moreover, the potential exists for implants to loosen due to an imprecise fit in the joint. This can be exacerbated by the sheer and impact forces experienced in a weight-bearing joint, such as a knee.

While there have been some efforts to utilize interpenetrating polymer networks (IPN) and semi-interpenetrating polymer network ("semi-IPN") structures, these efforts have generally failed to demonstrate successful adhesion to patient bone surfaces. While some polymers have shown success in providing low-friction durable surfaces that may simulate natural cartilage, these often have trouble bonding to bone structures as they heal. This can be problematic given the large amount of stress applied to osteochondral tissue.

SUMMARY

This summary is provided to comply with 37 C.F.R. § 1.73, require a summary of the invention briefly indicating the nature and substance of the invention. It is submitted with the understanding that it will not be used to interpret or limit the scope or meaning of the present disclosure.

A system for correcting an osteochondral defect is provided. The system comprises a tracking system comprising a probe having one or more probe tracking arrays, and one or more patient tracking arrays attached to a joint of a patient, wherein the tracking system is configured to collect surface data related to an articular surface of a bone of the joint. The system further comprises one or more processors configured to receive the surface data from the tracking system; define, based on the surface data, an outer boundary enclosing the osteochondral defect to designate a defect surface; generate, based on at least the surface data, a 3D bone model of the bone including a defect-free articular surface; and generate, based on at least the 3D bone model and the outer boundary, a 3D implant model corresponding to the defect surface. The system further comprises a manufacturing unit configured to manufacture an implant based on the 3D implant model.

According to some embodiments, the one or more processors are further configured to receive library data from a library of healthy bone anatomies; and apply the surface data and the library data to a statistical modeling equation to generate the 3D bone model.

According to some embodiments, a shape of an articular surface of the 3D implant model is based on at least a portion of the 3D bone model corresponding to the defect surface. According to additional embodiments, the shape of the articular surface of the 3D implant model is further based on at least a portion of the surface data corresponding to the defect surface. According to additional embodiments, the shape of the articular surface of the 3D implant model is further based on at least a thickness of articular cartilage of the joint.

According to some embodiments, the manufacturing unit is further configured to produce a standard implant by additive manufacturing; and refine the standard implant based on the 3D implant model by one or more machining techniques to produce the implant.

According to some embodiments, the implant comprises a first porous layer configured for bone ingrowth; a non-porous layer joined to the first porous layer; a second porous layer joined to the non-porous layer opposite the first porous layer; and a synthetic polymer material over-molded via an injection molding process to interlock with the pores in the second porous layer. According to additional embodiments, the first porous layer, the non-porous layer, and the second porous layer comprise one or more of titanium, tantalum, and stainless steel; and the polymer material comprises an interpenetrating polymer network including one or more of porous polyurethane, polyurethane, acrylonitrile butadiene styrene (ABS), polylactic acid (PLA), polylactic-co-glycolic acid) (PLGA), poly(ε-caprolactone) (PCL), polyether ether ketone (PEEK), poly(ethylene glycol) (PEG), ultra-high molecular weight polyethylene (UHMWPE), polyether urethane, chitosan, collagen, gelatin, polyacrylic acid (PAA), and polyglycolic acid (PGA).

According to some embodiments, the one or more processors are further configured to generate, based on the 3D bone model and the 3D implant model, an implantation plan comprising one or more characteristics of a cavity on the bone for receiving the implant. According to additional embodiments, the system further comprises a surgical system having a robotic arm configured to resect the bone to form the cavity based on the implantation plan.

A method of correcting an osteochondral defect is also provided. The method comprises collecting, by a probe, surface data related to an articular surface of a bone of a joint, wherein the articular surface comprises the osteochondral defect; generating, based on at least the surface data, a 3D bone model of the bone including a defect-free articular surface; defining, by the probe, an outer boundary enclosing the osteochondral defect to designate a defect surface; generating, based on at least the 3D bone model and the outer boundary, a 3D implant model corresponding to the defect surface; and manufacturing an implant based on the 3D implant model.

According to some embodiments, generating the 3D bone model is further based on library data from a library of healthy bone anatomies, and generating the 3D bone model comprises applying the surface data and the library data to a statistical modeling equation.

According to some embodiments, a shape of an articular surface of the 3D implant model is based on at least a portion of the 3D bone model corresponding to the defect surface. According to additional embodiments, the shape of the articular surface of the 3D implant model is further based on at least a portion of the surface data corresponding to the defect surface. According to additional embodiments, the shape of the articular surface of the 3D implant model is further based on at least a thickness of articular cartilage of the joint.

According to some embodiments, manufacturing an implant comprises producing a standard implant by additive manufacturing; and refining the standard implant based on the 3D implant model by one or more machining techniques.

According to some embodiments, the implant comprises a first porous layer configured for bone ingrowth; a non-porous layer joined to the first porous layer; a second porous layer joined to the non-porous layer opposite the first porous layer; and a synthetic polymer material over-molded via an injection molding process to interlock with the pores in the second porous layer. According to additional embodiments, the first porous layer, the non-porous layer, and the second porous layer comprise one or more of titanium, tantalum, and stainless steel; and the polymer material comprises an interpenetrating polymer network including one or more of porous polyurethane, polyurethane, acrylonitrile butadiene styrene (ABS), polylactic acid (PLA), polylactic-co-glycolic acid) (PLGA), poly(ε-caprolactone) (PCL), polyether ether ketone (PEEK), poly(ethylene glycol) (PEG), ultra-high molecular weight polyethylene (UHMWPE), polyether urethane, chitosan, collagen, gelatin, polyacrylic acid (PAA), and polyglycolic acid (PGA).

According to some embodiments, the method further comprises generating, based on the 3D bone model and the 3D implant model, an implantation plan comprising one or more characteristics of a cavity on the bone for receiving the implant; resecting the bone to form the cavity based on the implantation plan; and inserting the implant into the cavity based on the implantation plan.

According to some embodiments, the method further comprises injecting a fluid material around an outer surface of the implant, wherein the fluid material comprises one or more of chondrocytes, morselized bone, blood platelet concentrate, bone marrow, stem cells, growth factors, and extracellular matrix.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIG. 2C depicts an illustrative implementation in which a surgical computer is connected to a surgical data server via a network in accordance with an embodiment.

DETAILED DESCRIPTION

Figure 1:
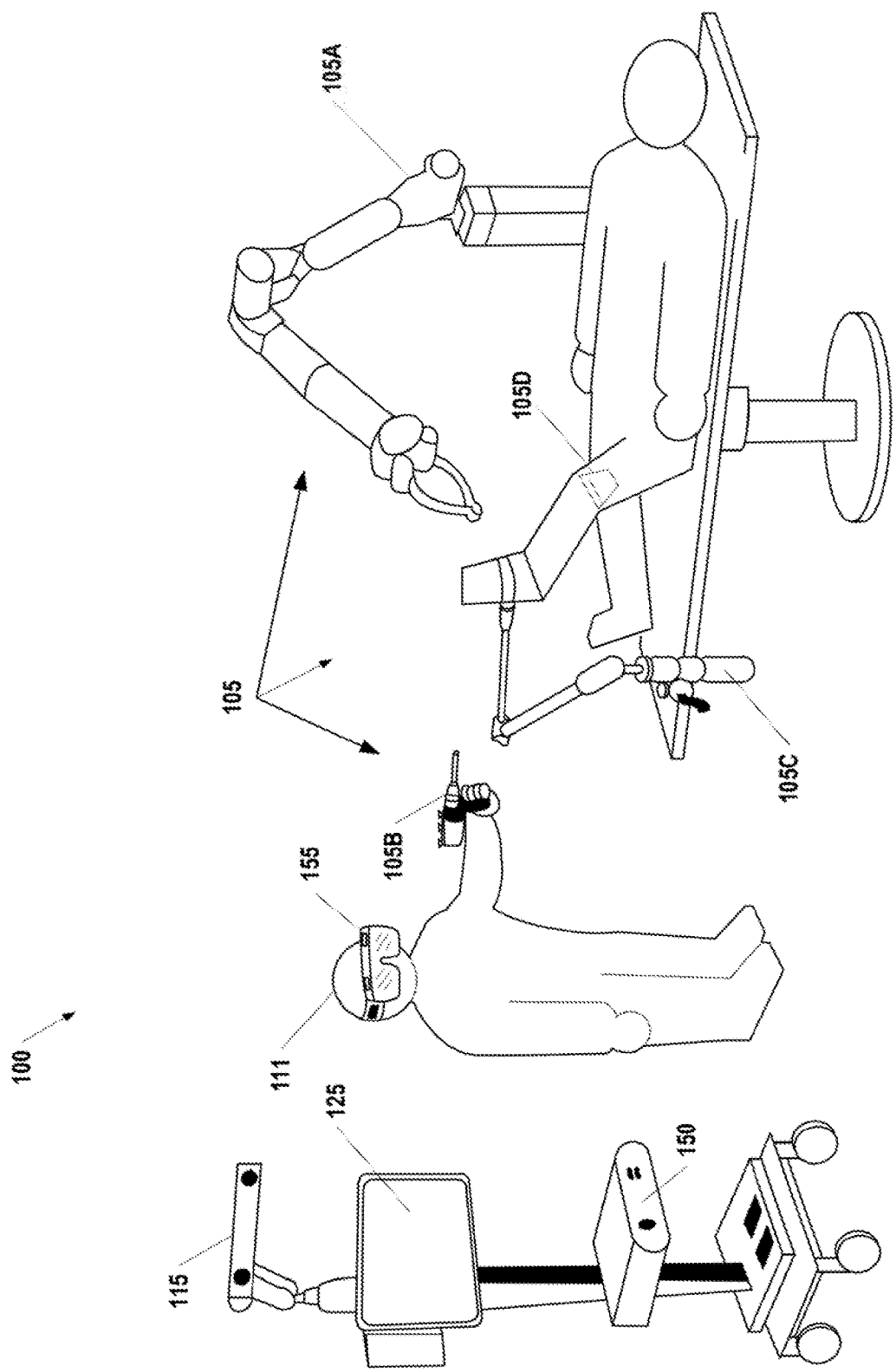
FIG. 1 depicts an operating theatre including an illustrative computer-assisted surgical system (CASS) in accordance with an embodiment.

The present disclosure describes patient-specific implants for the treatment of an OCD on a patient's joint, methods for the treatment of OCDs using such implants, and systems for treatment of OCDs using such implants.

In some embodiments, by combining the information obtained from mapping the surface of the patient's joint surrounding the OCD with a database of healthy bone anatomies, an implant may be installed that achieves a congruent and smooth articular surface and restores the contours of a healthy joint articular surface. In the following description, for purposes of explanation, numerous specific details are set forth in order to provide a thorough understanding of example embodiments. It will be evident to one skilled in the art, however, that embodiments can be practiced without these specific details.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this specification, the term "implant" is used to refer to a prosthetic device or structure manufactured to replace or enhance a biological structure, either permanently or on a trial basis. For example, in a knee replacement procedure, an implant can be placed on one or both of the tibia and the femur. While the term "implant" is generally considered to denote a man-made structure (as contrasted with a transplant), for the purposes of this specification, an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon could also apply, in some embodiments to a technician or nurse.

The systems, methods, and devices disclosed herein are particularly well adapted for surgical procedures that utilize surgical navigation systems, such as the NAVIO® surgical navigation system. NAVIO is a registered trademark of BLUE BELT TECHNOLOGIES, INC. of Pittsburgh, PA, which is a subsidiary of SMITH & NEPHEW, INC. of Memphis, TN.

CASS Ecosystem Overview

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a NAVIO® hand piece or a cutting guide or jig) or, alternatively, the End Effector 105B can include a device or instrument held or positioned by a Robotic Arm 105A. While one Robotic Arm 105A is illustrated in FIG. 1, in some embodiments there may be multiple devices. As examples, there may be one Robotic Arm 105A on each side of an operating table T or two devices on one side of the table T. The Robotic Arm 105A may be mounted directly to the table T, be located next to the table T on a floor platform (not shown), mounted on a floor-to-ceiling pole, or mounted on a wall or ceiling of an operating room. The floor platform may be fixed or moveable. In one particular embodiment, the Robotic Arm 105A is mounted on a floor-to-ceiling pole located between the patient's legs or feet. In some embodiments, the End Effector 105B may include a suture holder or a stapler to assist in closing wounds. Further, in the case of two Robotic Arms 105A, the surgical computer 150 can drive the Robotic Arms to work together to suture the wound at closure. Alternatively, the surgical computer 150 can drive one or more Robotic Arms 105A to staple the wound at closure.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table T or two devices on one side of the table T. The Limb Positioner 105C may be mounted directly to the table T, be located next to the table T on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light, and/or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 can also include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 can also be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the Tracking System 115, the surgical computer 150 can detect objects and prevent collision. For example, the surgical computer 150 can prevent the Robotic Arm 105A and/or the End Effector 105B from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the Robotic Arm 105A.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they can also be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient can also involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process can also include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 can also utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step can also utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intraoperatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode, RFID tag, or other method. In some embodiments, the powered impactor device may have a dual function. For example, the powered impactor device not only could provide reciprocating motion to provide an impact force, but also could provide reciprocating motion for a broach or rasp.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by surgeon.

In some embodiments, the powered impaction device includes feedback sensors that gather data during instrument use, and send data to a computing device such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 can also place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

The examples below describe uses of the robotic device in the context of a hip surgery; however, it should be understood that the robotic arm may have other applications for surgical procedures involving knees, shoulders, etc. One example of use of a robotic arm in the context of forming an anterior cruciate ligament (ACL) graft tunnel is described in U.S. Provisional Patent Application No. 62/723,898 filed Aug. 28, 2018 and entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, München, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561,048 to Nowatschin et al., and U.S. Pat. No. 10,342,636 to Nowatschin et al., the entire contents of each of which is herein incorporated by reference.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various aspects of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/818,531 filed Aug. 15, 2011 and entitled "Systems and Methods for Optimizing Parameters for Orthopaedic Procedures"; U.S. patent application Ser. No. 18/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 2C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 2A:
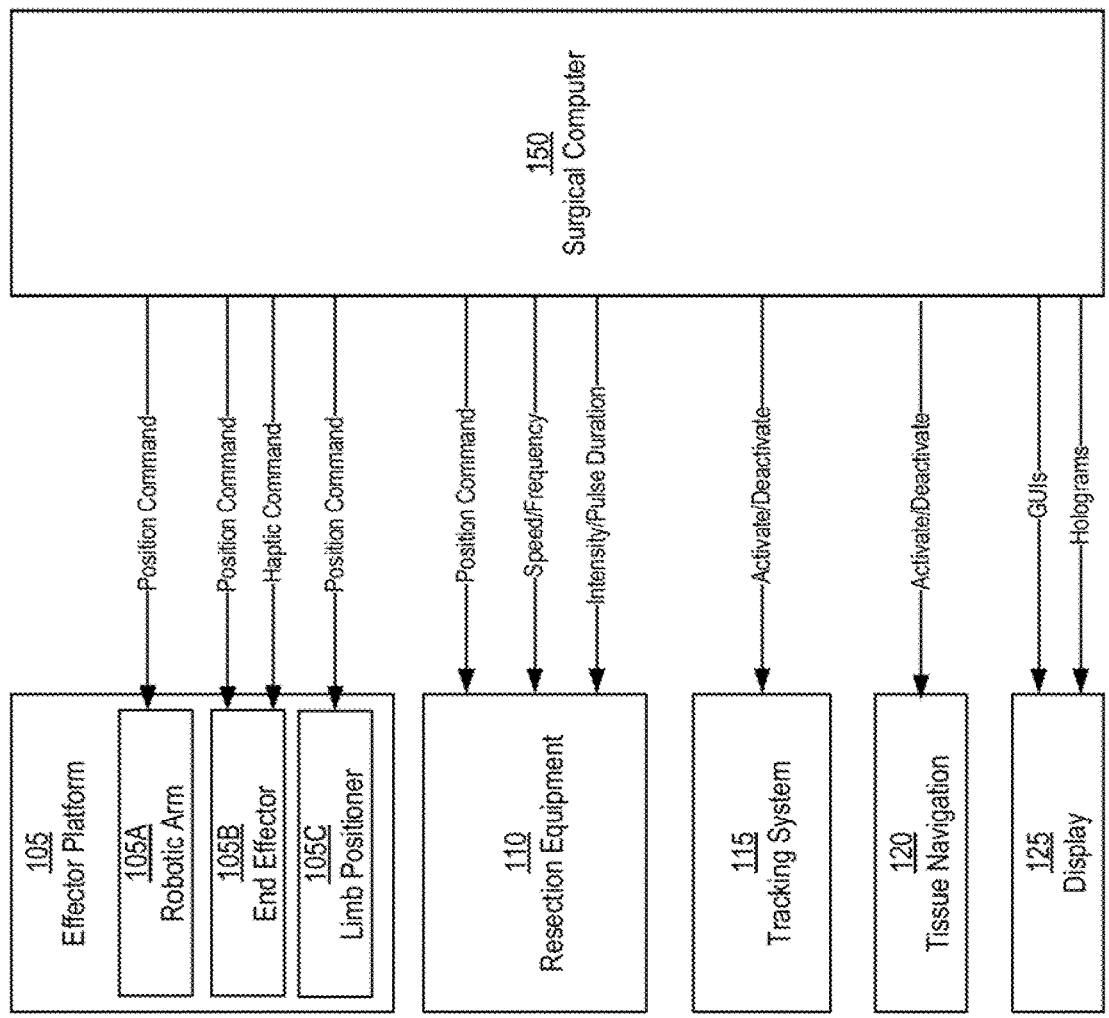
FIG. 2A depicts illustrative control instructions that a surgical computer provides to other components of a CASS in accordance with an embodiment.
Figure 2B:
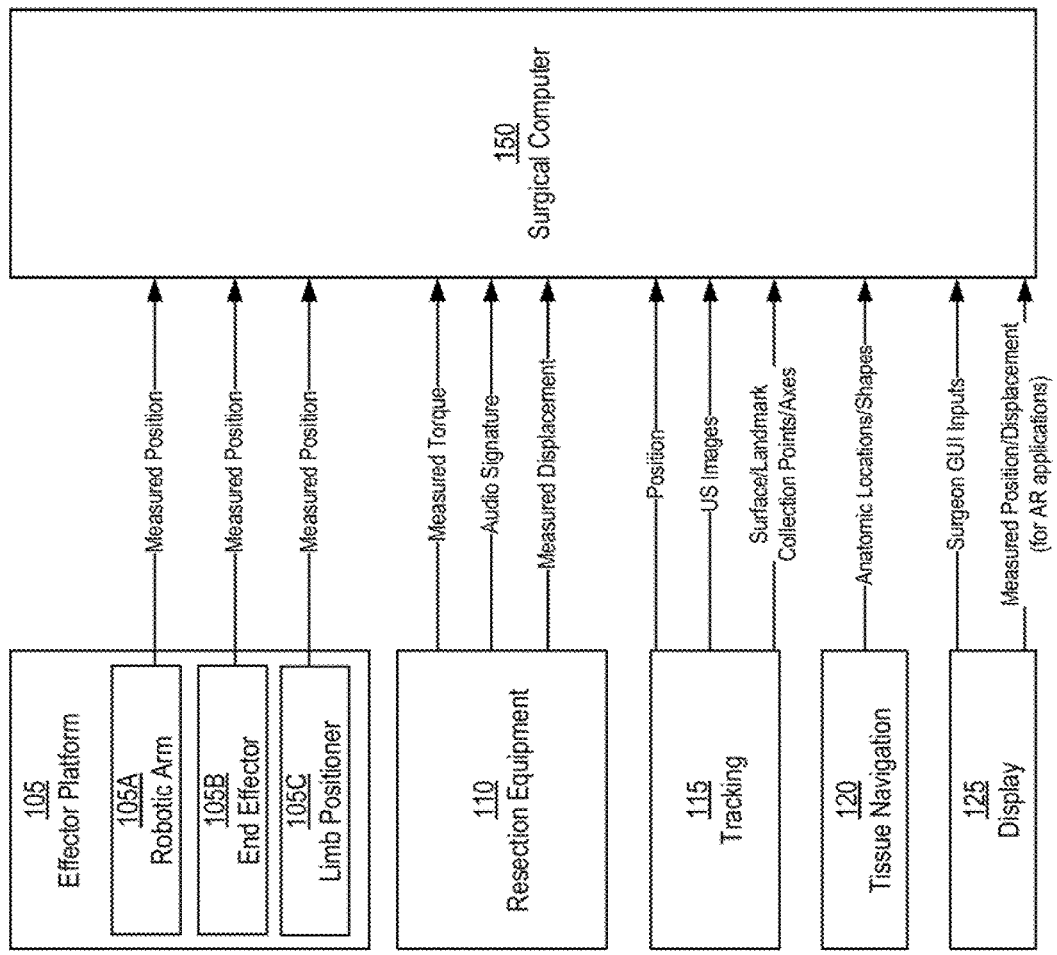
FIG. 2B depicts illustrative control instructions that components of a CASS provide to a surgical computer in accordance with an embodiment.

FIGS. 2A and 2B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 2A shows examples of some of the control instructions that the Surgical Computer 150 provides to other components of the CASS 100, according to some embodiments. Note that the example of FIG. 2A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 2A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 2A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc. using techniques known in the art. The display 125 can include various aspects of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict varus and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 can also include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 can also provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 can also preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 2C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in U.S. Provisional Patent Application No. 62/719,415 entitled "Patient Specific Surgical Method and System," the entirety of which is incorporated herein by reference.

FIG. 2B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 2B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQSD-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example, by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively. This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 into order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 2C.

FIG. 2C illustrates a "cloud-based" implementation in which the Surgical Computer 150 is connected to a Surgical Data Server 180 via a Network 175. This Network 175 may be, for example, a private intranet or the Internet. In addition to the data from the Surgical Computer 150, other sources can transfer relevant data to the Surgical Data Server 180. The example of FIG. 2C shows 3 additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170 may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, a SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design. Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 2C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc. to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 2A-2C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below, a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patient-centric set of indices may be used so that data pertaining to a particular patient or a set of patients similar to a particular patient can be readily extracted. This concept can be similarly applied to surgeons, implant characteristics, CASS component versions, etc.

Further details of the management of episode of care data is described in U.S. Patent Application No. 62/783,858 filed Dec. 21, 2018 and entitled "Methods and Systems for Providing an Episode of Care," the entirety of which is incorporated herein by reference.

Open Versus Closed Digital Ecosystems

In some embodiments, the CASS 100 is designed to operate as a self-contained or "closed" digital ecosystem. Each component of the CASS 100 is specifically designed to be used in the closed ecosystem, and data is generally not accessible to devices outside of the digital ecosystem. For example, in some embodiments, each component includes software or firmware that implements proprietary protocols for activities such as communication, storage, security, etc. The concept of a closed digital ecosystem may be desirable for a company that wants to control all components of the CASS 100 to ensure that certain compatibility, security, and reliability standards are met. For example, the CASS 100 can be designed such that a new component cannot be used with the CASS unless it is certified by the company.

In other embodiments, the CASS 100 is designed to operate as an "open" digital ecosystem. In these embodiments, components may be produced by a variety of different companies according to standards for activities, such as communication, storage, and security. Thus, by using these standards, any company can freely build an independent, compliant component of the CASS platform. Data may be transferred between components using publicly available application programming interfaces (APIs) and open, shareable data formats.

To illustrate one type of recommendation that may be performed with the CASS 100, a technique for optimizing surgical parameters is disclosed below. The term "optimization" in this context means selection of parameters that are optimal based on certain specified criteria. In an extreme case, optimization can refer to selecting optimal parameter(s) based on data from the entire episode of care, including any pre-operative data, the state of CASS data at a given point in time, and post-operative goals. Moreover, optimization may be performed using historical data, such as data generated during past surgeries involving, for example, the same surgeon, past patients with physical characteristics similar to the current patient, or the like.

The optimized parameters may depend on the portion of the patient's anatomy to be operated on. For example, for knee surgeries, the surgical parameters may include positioning information for the femoral and tibial component including, without limitation, rotational alignment (e.g., varus/valgus rotation, external rotation, flexion rotation for the femoral component, posterior slope of the tibial component), resection depths (e.g., varus knee, valgus knee), and implant type, size and position. The positioning information may further include surgical parameters for the combined implant, such as overall limb alignment, combined tibiofemoral hyperextension, and combined tibiofemoral resection. Additional examples of parameters that could be optimized for a given TKA femoral implant by the CASS 100 include the following:

| Parameter | Reference | Exemplary Recommendation (s) |
| --- | --- | --- |
| Size | Posterior | The largest sized implant that does not overhang medial/lateral bone edges or overhang the anterior femur. A size that does not result in overstuffing the patella femoral joint |
| Implant Position - Medial Lateral | Medial/lateral cortical bone edges | Center the implant evenly between the medial/lateral cortical bone edges |
| Resection Depth - Varus Knee | Distal and posterior lateral | 6 mm of bone |
| Resection Depth - Valgus Knee | Distal and posterior medial | 7 mm of bone |
| Rotation - Varus/Valgus | Mechanical Axis | 1° varus |
| Rotation - External | Transepicondylar Axis | 1° external from the transepicondylar axis |
| Rotation - Flexion | Mechanical Axis | 3° flexed |

Additional examples of parameters that could be optimized for a given TKA tibial implant by the CASS 100 include the following:

| Parameter | Reference | Exemplary Recommendation (s) |
|---|---|---|
| Size | Posterior | The largest sized implant that does not overhang the medial, lateral, anterior, and posterior tibial edges |
| Implant Position | Medial/lateral and anterior/posterior cortical bone edges | Center the implant evenly between the medial/lateral and anterior/posterior cortical bone edges |
| Resection Depth - Varus Knee | Lateral/Medial | 4 mm of bone |
| Resection Depth - Valgus Knee | Lateral/Medial | 5 mm of bone |
| Rotation - Varus/Valgus | Mechanical Axis | 1° valgus |
| Rotation - External | Tibial Anterior Posterior Axis | 1° external from the tibial anterior paxis |
| Posterior Slope | Mechanical Axis | 3° posterior slope |

For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Shoulder parameters may include, without limitation, humeral resection depth/angle, humeral stem version, humeral offset, glenoid version and inclination, as well as reverse shoulder parameters such as humeral resection depth/angle, humeral stem version, Glenoid tilt/version, glenosphere orientation, glenosphere offset and offset direction.

Various conventional techniques exist for optimizing surgical parameters. However, these techniques are typically computationally intensive and, thus, parameters often need to be determined pre-operatively. As a result, the surgeon is limited in his or her ability to make modifications to optimized parameters based on issues that may arise during surgery. Moreover, conventional optimization techniques typically operate in a "black box" manner with little or no explanation regarding recommended parameter values. Thus, if the surgeon decides to deviate from a recommended parameter value, the surgeon typically does so without a full understanding of the effect of that deviation on the rest of the surgical workflow, or the impact of the deviation on the patient's post-surgery quality of life.

Operative Patient Care System

Figure 3:
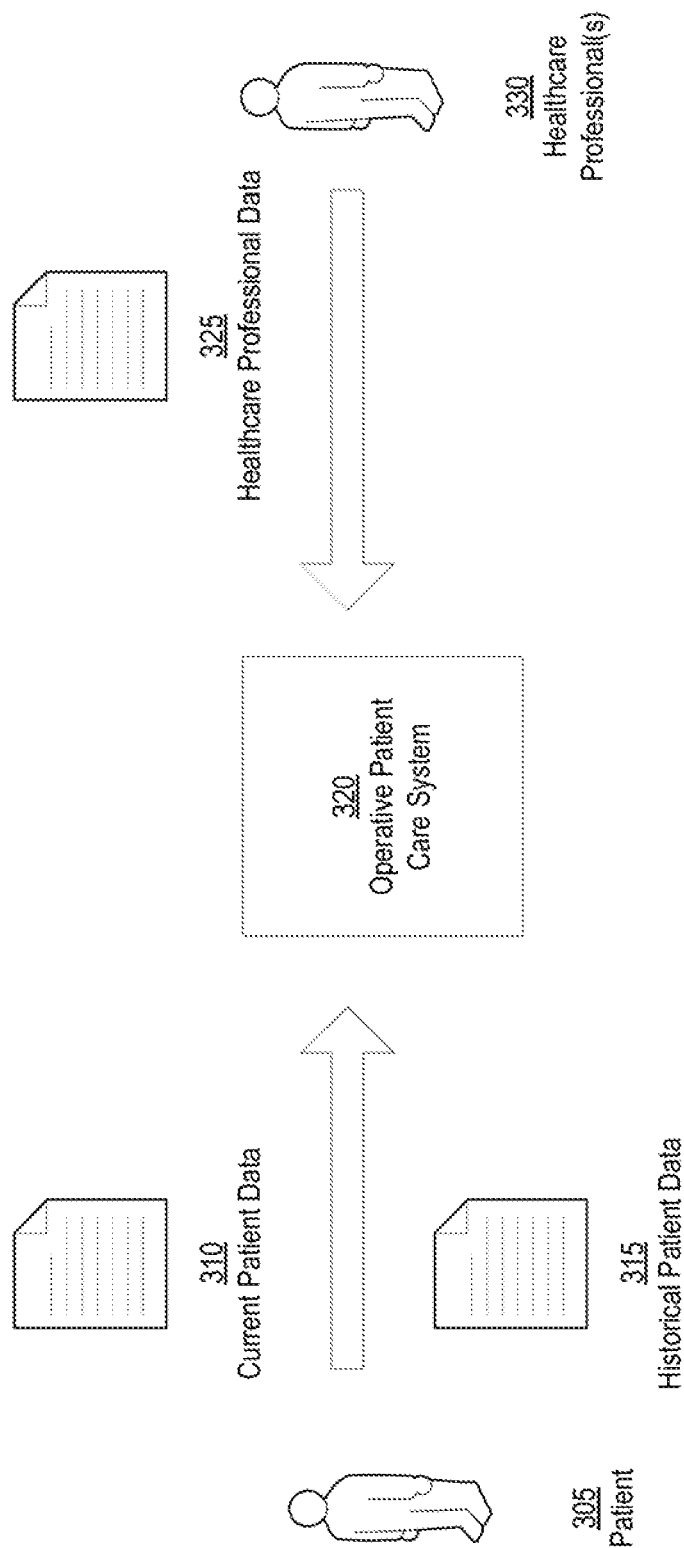
FIG. 3 depicts an operative patient care system and illustrative data sources in accordance with an embodiment.

The general concepts of optimization may be extended to the entire episode of care using an Operative Patient Care System 320 that uses the surgical data, and other data from the Patient 305 and Healthcare Professionals 330 to optimize outcomes and patient satisfaction as depicted in FIG. 3.

Conventionally, pre-operative diagnosis, pre-operative surgical planning, intra-operative execution of a prescribed plan, and post-operative management of total joint arthroplasty are based on individual experience, published literature, and training knowledge bases of surgeons (ultimately, tribal knowledge of individual surgeons and their 'network' of peers and journal publications) and their native ability to make accurate intra-operative tactile discernment of "balance" and accurate manual execution of planar resections using guides and visual cues. This existing knowledge base and execution is limited with respect to the outcomes optimization offered to patients needing care. For example, limits exist with respect to accurately diagnosing a patient to the proper, least-invasive prescribed care; aligning dynamic patient, healthcare economic, and surgeon preferences with patient-desired outcomes; executing a surgical plan resulting in proper bone alignment and balance, etc.; and receiving data from disconnected sources having different biases that are difficult to reconcile into a holistic patient framework. Accordingly, a data-driven tool that more accurately models anatomical response and guides the surgical plan can improve the existing approach.

The Operative Patient Care System 320 is designed to utilize patient specific data, surgeon data, healthcare facility data, and historical outcome data to develop an algorithm that suggests or recommends an optimal overall treatment plan for the patient's entire episode of care (preoperative, operative, and postoperative) based on a desired clinical outcome. For example, in one embodiment, the Operative Patient Care System 320 tracks adherence to the suggested or recommended plan, and adapts the plan based on patient/care provider performance. Once the surgical treatment plan is complete, collected data is logged by the Operative Patient Care System 320 in a historical database. This database is accessible for future patients and the development of future treatment plans. In addition to utilizing statistical and mathematical models, simulation tools (e.g., LIFEMOD®) can be used to simulate outcomes, alignment, kinematics, etc. based on a preliminary or proposed surgical plan, and reconfigure the preliminary or proposed plan to achieve desired or optimal results according to a patient's profile or a surgeon's preferences. The Operative Patient Care System 320 ensures that each patient is receiving personalized surgical and rehabilitative care, thereby improving the chance of successful clinical outcomes and lessening the economic burden on the facility associated with near-term revision.

In some embodiments, the Operative Patient Care System 320 employs a data collecting and management method to provide a detailed surgical case plan with distinct steps that are monitored and/or executed using a CASS 100. The performance of the user(s) is calculated at the completion of each step and can be used to suggest changes to the subsequent steps of the case plan. Case plan generation relies on a series of input data that is stored on a local or cloud-storage database. Input data can be related to both the current patient undergoing treatment and historical data from patients who have received similar treatment(s).

A Patient 305 provides inputs such as Current Patient Data 310 and Historical Patient Data 315 to the Operative Patient Care System 320. Various methods generally known in the art may be used to gather such inputs from the Patient 305. For example, in some embodiments, the Patient 305 fills out a paper or digital survey that is parsed by the Operative Patient Care System 320 to extract patient data. In other embodiments, the Operative Patient Care System 320 may extract patient data from existing information sources, such as electronic medical records (EMRs), health history files, and payer/provider historical files. In still other embodiments, the Operative Patient Care System 320 may provide an application program interface (API) that allows the external data source to push data to the Operative Patient Care System. For example, the Patient 305 may have a mobile phone, wearable device, or other mobile device that collects data (e.g., heart rate, pain or discomfort levels, exercise or activity levels, or patient-submitted responses to the patient's adherence with any number of pre-operative plan criteria or conditions) and provides that data to the Operative Patient Care System 320. Similarly, the Patient 305 may have a digital application on his or her mobile or wearable device that enables data to be collected and transmitted to the Operative Patient Care System 320.

Current Patient Data 310 can include, but is not limited to, activity level, preexisting conditions, comorbidities, prehab performance, health and fitness level, pre-operative expectation level (relating to hospital, surgery, and recovery), a Metropolitan Statistical Area (MSA) driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), and an indication of the expected ideal outcome of the procedure.

Historical Patient Data 315 can include, but is not limited to, activity level, preexisting conditions, comorbidities, prehab performance, health and fitness level, pre-operative expectation level (relating to hospital, surgery, and recovery), a MSA driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), expected ideal outcome of the procedure, actual outcome of the procedure (patient reported outcomes [PROs], survivorship of implants, pain levels, activity levels, etc.), sizes of implants used, position/orientation/alignment of implants used, soft-tissue balance achieved, etc.

Healthcare Professional(s) 330 conducting the procedure or treatment may provide various types of data 325 to the Operative Patient Care System 320. This Healthcare Professional Data 325 may include, for example, a description of a known or preferred surgical technique (e.g., Cruciate Retaining (CR) vs Posterior Stabilized (PS), up-vs downsizing, tourniquet vs tourniquet-less, femoral stem style, preferred approach for THA, etc.), the level of training of the Healthcare Professional(s) 330 (e.g., years in practice, fellowship trained, where they trained, whose techniques they emulate), previous success level including historical data (outcomes, patient satisfaction), and the expected ideal outcome with respect to range of motion, days of recovery, and survivorship of the device. The Healthcare Professional Data 325 can be captured, for example, with paper or digital surveys provided to the Healthcare Professional 330, via inputs to a mobile application by the Healthcare Professional, or by extracting relevant data from EMRs. In addition, the CASS 100 may provide data such as profile data (e.g., a Patient Specific Knee Instrument Profile) or historical logs describing use of the CASS during surgery.

Information pertaining to the facility where the procedure or treatment will be conducted may be included in the input data. This data can include, without limitation, the following: Ambulatory Surgery Center (ASC) vs hospital, facility trauma level, Comprehensive Care for Joint Replacement Program (CJR) or bundle candidacy, a MSA driven score, community vs metro, academic vs non-academic, postoperative network access (Skilled Nursing Facility [SNF] only, Home Health, etc.), availability of medical professionals, implant availability, and availability of surgical equipment.

These facility inputs can be captured by, for example and without limitation, Surveys (Paper/Digital), Surgery Scheduling Tools (e.g., apps, Websites, Electronic Medical Records [EMRs], etc.), Databases of Hospital Information (on the Internet), etc. Input data relating to the associated healthcare economy including, but not limited to, the socioeconomic profile of the patient, the expected level of reimbursement the patient will receive, and if the treatment is patient specific may also be captured.

These healthcare economic inputs can be captured by, for example and without limitation, Surveys (Paper/Digital), Direct Payer Information, Databases of Socioeconomic status (on the Internet with zip code), etc. Finally, data derived from simulation of the procedure is captured. Simulation inputs include implant size, position, and orientation. Simulation can be conducted with custom or commercially available anatomical modeling software programs (e.g., LIFE-MOD®, AnyBody, or OpenSIM). It is noted that the data inputs described above may not be available for every patient, and the treatment plan will be generated using the data that is available.

Prior to surgery, the Patient Data 310, 315 and Healthcare Professional Data 325 may be captured and stored in a cloud-based or online database (e.g., the Surgical Data Server 180 shown in FIG. 2C). Information relevant to the procedure is supplied to a computing system via wireless data transfer or manually with the use of portable media storage. The computing system is configured to generate a case plan for use with a CASS 100. Case plan generation will be described hereinafter. It is noted that the system has access to historical data from previous patients undergoing treatment, including implant size, placement, and orientation as generated by a computer-assisted, patient-specific knee instrument (PSKI) selection system, or automatically by the CASS 100 itself. To achieve this, case log data is uploaded to the historical database by a surgical sales rep or case engineer using an online portal. In some embodiments, data transfer to the online database is wireless and automated.

Historical data sets from the online database are used as inputs to a machine learning model such as, for example, a recurrent neural network (RNN) or other form of artificial neural network. As is generally understood in the art, an artificial neural network functions similar to a biologic neural network and is comprised of a series of nodes and connections. The machine learning model is trained to predict one or more values based on the input data. For the sections that follow, it is assumed that the machine learning model is trained to generate predictor equations. These predictor equations may be optimized to determine the optimal size, position, and orientation of the implants to achieve the best outcome or satisfaction level.

Once the procedure is complete, all patient data and available outcome data, including the implant size, position and orientation determined by the CASS 100, are collected and stored in the historical database. Any subsequent calculation of the target equation via the RNN will include the data from the previous patient in this manner, allowing for continuous improvement of the system.

In addition to, or as an alternative to determining implant positioning, in some embodiments, the predictor equation and associated optimization can be used to generate the resection planes for use with a PSKI system. When used with a PSKI system, the predictor equation computation and optimization are completed prior to surgery. Patient anatomy is estimated using medical image data (x-ray, CT, MRI). Global optimization of the predictor equation can provide an ideal size and position of the implant components. Boolean intersection of the implant components and patient anatomy is defined as the resection volume. PSKI can be produced to remove the optimized resection envelope. In this embodiment, the surgeon cannot alter the surgical plan intraoperatively.

The surgeon may choose to alter the surgical case plan at any time prior to or during the procedure. If the surgeon elects to deviate from the surgical case plan, the altered size, position, and/or orientation of the component(s) is locked, and the global optimization is refreshed based on the new size, position, and/or orientation of the component(s) (using the techniques previously described) to find the new ideal position of the other component(s) and the corresponding resections needed to be performed to achieve the newly optimized size, position and/or orientation of the component(s). For example, if the surgeon determines that the size, position and/or orientation of the femoral implant in a TKA needs to be updated or modified intraoperatively, the femoral implant position is locked relative to the anatomy, and the new optimal position of the tibia will be calculated (via global optimization) considering the surgeon's changes to the femoral implant size, position and/or orientation. Furthermore, if the surgical system used to implement the case plan is robotically assisted (e.g., as with NAVIO® or the MAKO Rio), bone removal and bone morphology during the surgery can be monitored in real time. If the resections made during the procedure deviate from the surgical plan, the subsequent placement of additional components may be optimized by the processor taking into account the actual resections that have already been made.

Figure 4A:
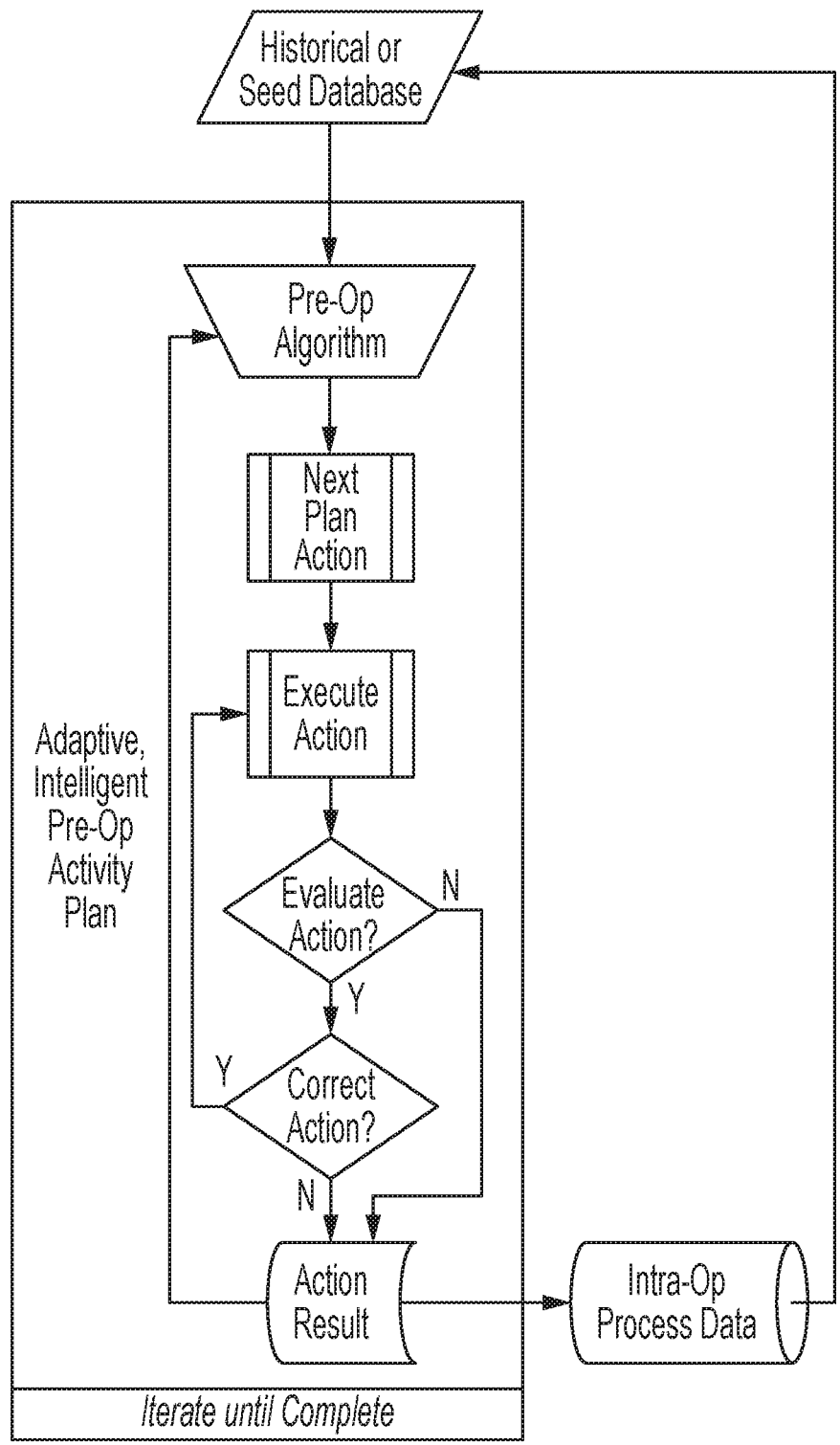
FIG. 4A depicts an illustrative flow diagram for determining a pre-operative surgical plan in accordance with an embodiment.
Figure 4B:
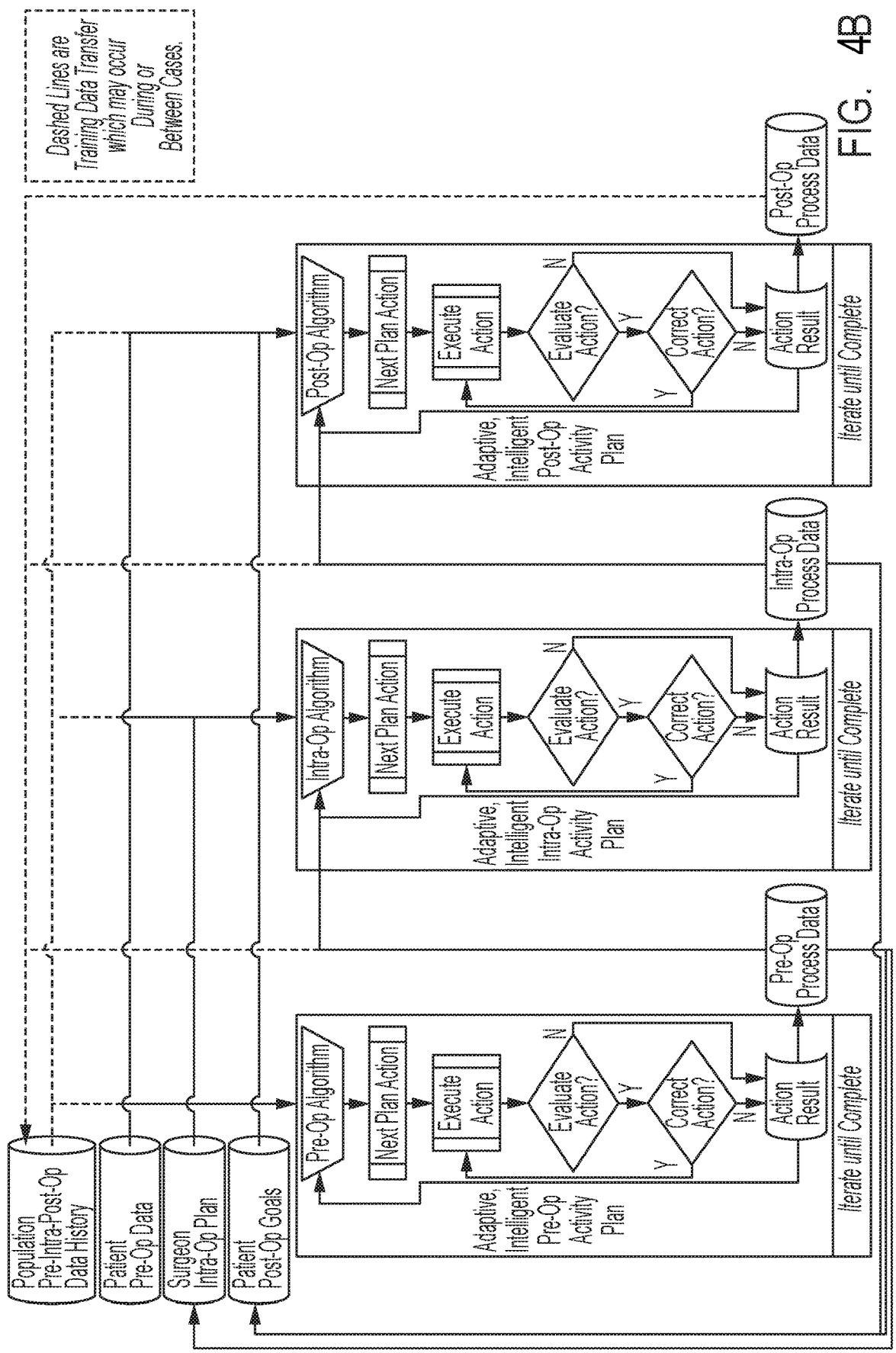
FIG. 4B depicts an illustrative flow diagram for determining an episode of care including pre-operative, intraoperative, and post-operative actions in accordance with an embodiment.

FIG. 4A illustrates how the Operative Patient Care System 320 may be adapted for performing case plan matching services. In this example, data is captured relating to the current patient 310 and is compared to all or portions of a historical database of patient data and associated outcomes 315. For example, the surgeon may elect to compare the plan for the current patient against a subset of the historical database. Data in the historical database can be filtered to include, for example, only data sets with favorable outcomes, data sets corresponding to historical surgeries of patients with profiles that are the same or similar to the current patient profile, data sets corresponding to a particular surgeon, data sets corresponding to a particular aspect of the surgical plan (e.g., only surgeries where a particular ligament is retained), or any other criteria selected by the surgeon or medical professional. If, for example, the current patient data matches or is correlated with that of a previous patient who experienced a good outcome, the case plan from the previous patient can be accessed and adapted or adopted for use with the current patient. The predictor equation may be used in conjunction with an intra-operative algorithm that identifies or determines the actions associated with the case plan. Based on the relevant and/or preselected information from the historical database, the intra-operative algorithm determines a series of recommended actions for the surgeon to perform. Each execution of the algorithm produces the next action in the case plan. If the surgeon performs the action, the results are evaluated. The results of the surgeon's performing the action are used to refine and update inputs to the intra-operative algorithm for generating the next step in the case plan. Once the case plan has been fully executed all data associated with the case plan, including any deviations performed from the recommended actions by the surgeon, are stored in the database of historical data. In some embodiments, the system utilizes preoperative, intraoperative, or postoperative modules in a piecewise fashion, as opposed to the entire continuum of care. In other words, caregivers can prescribe any permutation or combination of treatment modules including the use of a single module. These concepts are illustrated in FIG. 4B and can be applied to any type of surgery utilizing the CASS 100.

Surgery Process Display

As noted above with respect to FIGS. 1-2C, the various components of the CASS 100 generate detailed data records during surgery. The CASS 100 can track and record various actions and activities of the surgeon during each step of the surgery and compare actual activity to the pre-operative or intraoperative surgical plan. In some embodiments, a software tool may be employed to process this data into a format where the surgery can be effectively "played-back." For example, in one embodiment, one or more GUIs may be used that depict all of the information presented on the Display 125 during surgery. This can be supplemented with graphs and images that depict the data collected by different tools. For example, a GUI that provides a visual depiction of the knee during tissue resection may provide the measured torque and displacement of the resection equipment adjacent to the visual depiction to better provide an understanding of any deviations that occurred from the planned resection area. The ability to review a playback of the surgical plan or toggle between different aspects of the actual surgery vs. the surgical plan could provide benefits to the surgeon and/or surgical staff, allowing such persons to identify any deficiencies or challenging aspects of a surgery so that they can be modified in future surgeries. Similarly, in academic settings, the aforementioned GUIs can be used as a teaching tool for training future surgeons and/or surgical staff. Additionally, because the data set effectively records many aspects of the surgeon's activity, it may also be used for other reasons (e.g., legal or compliance reasons) as evidence of correct or incorrect performance of a particular surgical procedure.

Over time, as more and more surgical data is collected, a rich library of data may be acquired that describes surgical procedures performed for various types of anatomy (knee, shoulder, hip, etc.) by different surgeons for different patients. Moreover, aspects such as implant type and dimension, patient demographics, etc. can further be used to enhance the overall dataset. Once the dataset has been established, it may be used to train a machine learning model (e.g., RNN) to make predictions of how surgery will proceed based on the current state of the CASS 100.

Training of the machine learning model can be performed as follows. The overall state of the CASS 100 can be sampled over a plurality of time periods for the duration of the surgery. The machine learning model can then be trained to translate a current state at a first time period to a future state at a different time period. By analyzing the entire state of the CASS 100 rather than the individual data items, any causal effects of interactions between different components of the CASS 100 can be captured. In some embodiments, a plurality of machine learning models may be used rather than a single model. In some embodiments, the machine learning model may be trained not only with the state of the CASS 100, but also with patient data (e.g., captured from an EMR) and an identification of members of the surgical staff. This allows the model to make predictions with even greater specificity. Moreover, it allows surgeons to selectively make predictions based only on their own surgical experiences if desired.

Figure 4C:
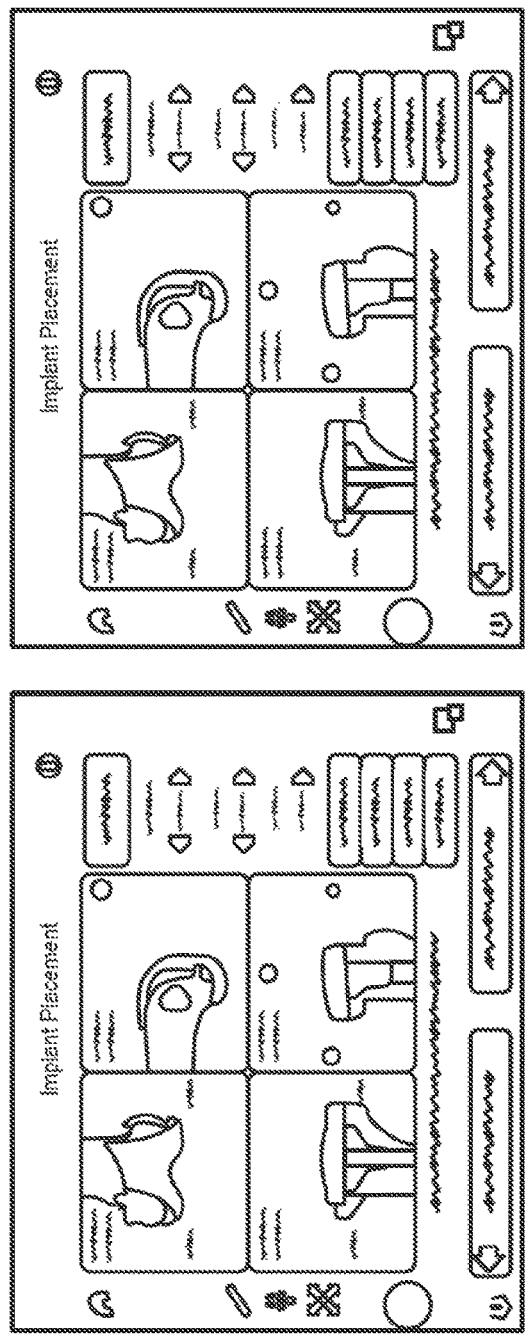
FIG. 4C depicts illustrative graphical user interfaces including images depicting an implant placement in accordance with an embodiment.
Figure 4C:
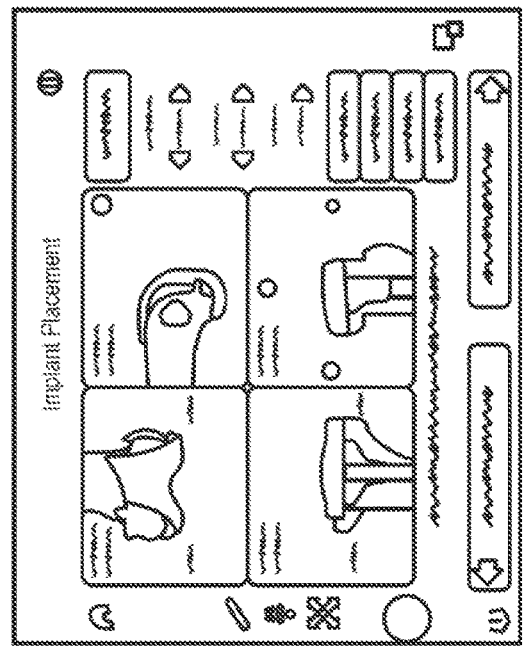

In some embodiments, predictions or recommendations made by the aforementioned machine learning models can be directly integrated into the surgical workflow. For example, in some embodiments, the Surgical Computer 150 may execute the machine learning model in the background making predictions or recommendations for upcoming actions or surgical conditions. A plurality of states can thus be predicted or recommended for each period. For example, the Surgical Computer 150 may predict or recommend the state for the next 5 minutes in 30 second increments. Using this information, the surgeon can utilize a "process display" view of the surgery that allows visualization of the future state. For example, FIG. 4C depicts a series of images that may be displayed to the surgeon depicting the implant placement interface. The surgeon can cycle through these images, for example, by entering a particular time into the display 125 of the CASS 100 or instructing the system to advance or rewind the display in a specific time increment using a tactile, oral, or other instruction. In one embodiment, the process display can be presented in the upper portion of the surgeon's field of view in the AR HMD. In some embodiments, the process display can be updated in real-time. For example, as the surgeon moves resection tools around the planned resection area, the process display can be updated so that the surgeon can see how his or her actions are affecting the other aspects of the surgery.

In some embodiments, rather than simply using the current state of the CASS 100 as an input to the machine learning model, the inputs to the model may include a planned future state. For example, the surgeon may indicate that he or she is planning to make a particular bone resection of the knee joint. This indication may be entered manually into the Surgical Computer 150 or the surgeon may verbally provide the indication. The Surgical Computer 150 can then produce a film strip showing the predicted effect of the cut on the surgery. Such a film strip can depict over specific time increments how the surgery will be affected, including, for example, changes in the patient's anatomy, changes to implant position and orientation, and changes regarding surgical intervention and instrumentation, if the contemplated course of action were to be performed. A surgeon or medical professional can invoke or request this type of film strip at any point in the surgery to preview how a contemplated course of action would affect the surgical plan if the contemplated action were to be carried out.

It should be further noted that, with a sufficiently trained machine learning model and robotic CASS, various aspects of the surgery can be automated such that the surgeon only needs to be minimally involved, for example, by only providing approval for various steps of the surgery. For example, robotic control using arms or other means can be gradually integrated into the surgical workflow over time with the surgeon slowly becoming less and less involved with manual interaction versus robot operation. The machine learning model in this case can learn what robotic commands are required to achieve certain states of the CASS-implemented plan. Eventually, the machine learning model may be used to produce a film strip or similar view or display that predicts and can preview the entire surgery from an initial state. For example, an initial state may be defined that includes the patient information, the surgical plan, implant characteristics, and surgeon preferences. Based on this information, the surgeon could preview an entire surgery to confirm that the CASS-recommended plan meets the surgeon's expectations and/or requirements. Moreover, because the output of the machine learning model is the state of the CASS 100 itself, commands can be derived to control the components of the CASS to achieve each predicted state. In the extreme case, the entire surgery could thus be automated based on just the initial state information.

Using the Point Probe to Acquire High-Resolution of Key Areas During Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. Provisional Patent Application No. 62/658,988, filed Apr. 17, 2018 and entitled "Three Dimensional Guide with Selective Bone Matching," the entirety of which is incorporated herein by reference.

For hip applications, the point probe painting can be used to acquire high resolution data in key areas such as the acetabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as reference point to align the femoral component during hip arthroplasty. The alignment is highly dependent on proper location of the GT; thus, in some embodiments, the point probe is used to paint the GT to provide a high resolution view of the area. Similarly, in some embodiments, it may be useful to have a high-resolution view of the Lesser Trochanter (LT). For example, during hip arthroplasty, the Don Classification helps to select a stem that will maximize the ability of achieving a press-fit during surgery to prevent micromotion of femoral components post-surgery and ensure optimal bony ingrowth. As is generally understood in the art, the Dorr Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data could also be used for a navigated resurfacing procedure where the software/hardware aids the surgeon in preparing the proximal femur and placing the femoral component. As is generally understood in the art, during hip resurfacing, the femoral head and neck are not removed; rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-Operative Data to Patient Anatomy Using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light inferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

Osteochondral Implants

Figure 5:
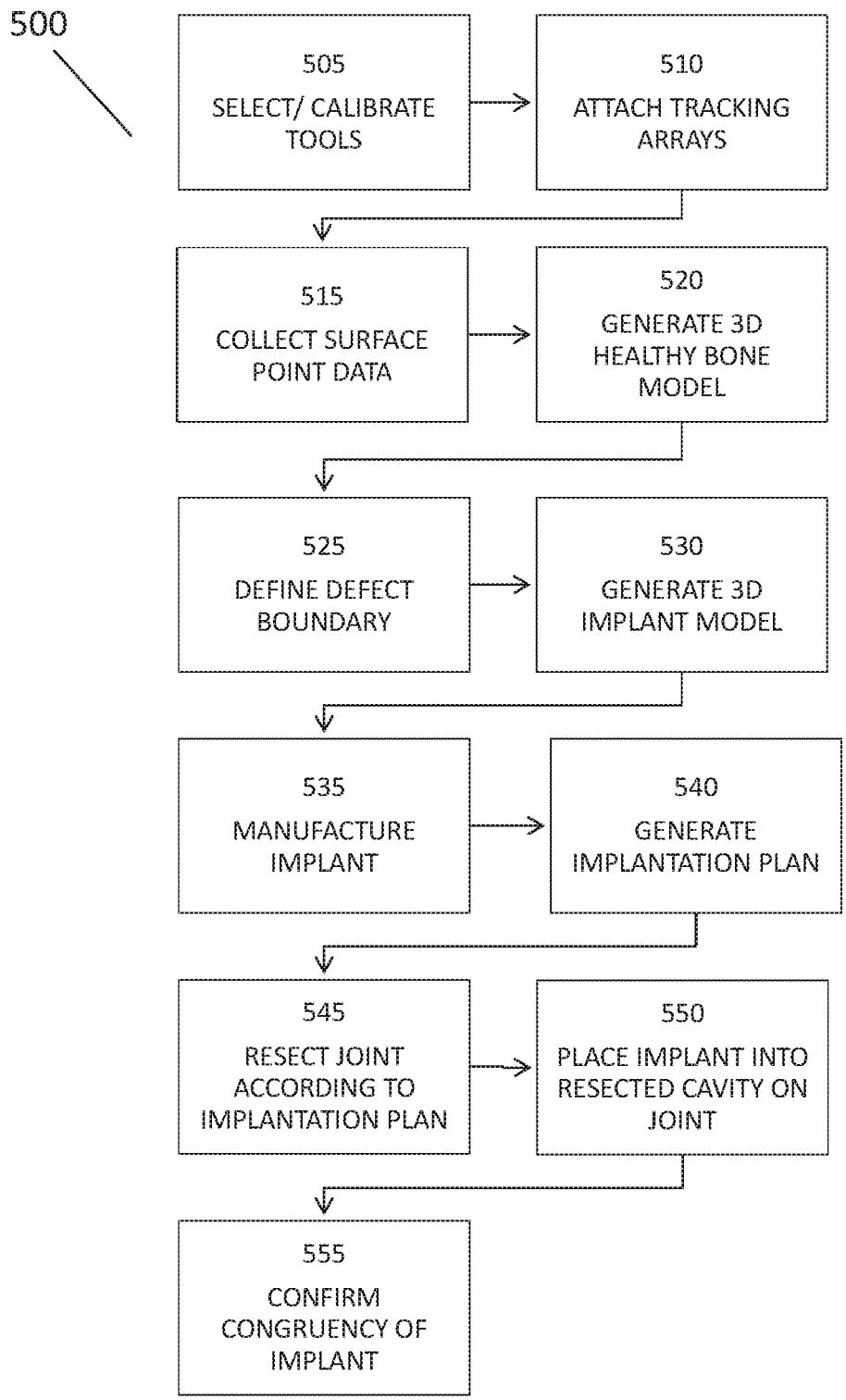
FIG. 5 depicts a flow diagram of an image-free method for treatment of an OCD of a joint in accordance with an embodiment.

In some embodiments, an osteochondral implant can be custom, semi-custom, or custom-selected from several available sizes and shapes. FIG. 5 is a flow diagram of an illustrative method for treatment of an osteochondral defect of a joint. Exemplary method 500 facilitates creation of a 3D model of the ideal osteochondral surface to be generated and allows an implantation plan to be created. This plan can include selection of an available implant or creation of a custom implant before surgery, depending on the level of customization in the embodiment. Method 500 includes operations such as select/calibrate tools 505, attach tracking arrays 510, collect surface point data 515, generate 3D healthy bone model 520, define defect boundary 525, generate 3D implant model 530, manufacture implant 535, generate implantation plan 540, resect joint according to implantation plan 545, place implant in resected cavity on joint 550, and confirm congruency of implant 555. The method 500 can be performed with more or fewer operations in certain examples. In an embodiment, one or more operations can be performed concurrently. In an embodiment, one or more operations can be performed intraoperatively. In an embodiment, one or more operations may be performed preoperatively.

As illustrated in step 505, the one or more tools used to collect surface point data are calibrated. In an embodiment, the one or more tools include an instrumented probe. In an embodiment, the one or more tools include a handpiece of a robotic surgical system. In an embodiment, the one or more tools include a location tracking system.

As illustrated in step 510, tracking arrays are attached to a portion of the anatomy of a patient on which the defect is located. In an embodiment, the tracking arrays are optical tracking arrays. In an embodiment, the patient's anatomy may be a knee. In an embodiment, the tracking arrays may be attached to one or more of the patient's femur and tibia. In an alternative embodiment, the patient's anatomy may be an ankle, a hip, a shoulder, spine, wrist, or an elbow.

As illustrated in step 515, an instrumented probe is used to collect surface point data to map the articular surface of the joint on which the defect is located. In an embodiment, the instrumented probe may map only the portion of the articular surface of the joint having healthy bone tissue. In an embodiment, the instrumented probe may map the articular surface of the joint using Cartesian coordinates, spherical coordinates, cylindrical coordinates, or any other suitable coordinate system. In an embodiment, mapping the articular surface of the joint is performed intraoperatively. In an embodiment, mapping the articular surface of the joint is performed preoperatively.

In some embodiments, the instrumented probe has a blunt tip so as to reduce the risk of piercing healthy cartilage. The blunt tip may have a radius from about 3 mm to about 10 mm. In an additional embodiment, the blunt tip may have a radius from about 4 mm to about 6 mm. In one embodiment, the blunt tip has a radius of 4 mm.

Figure 6:
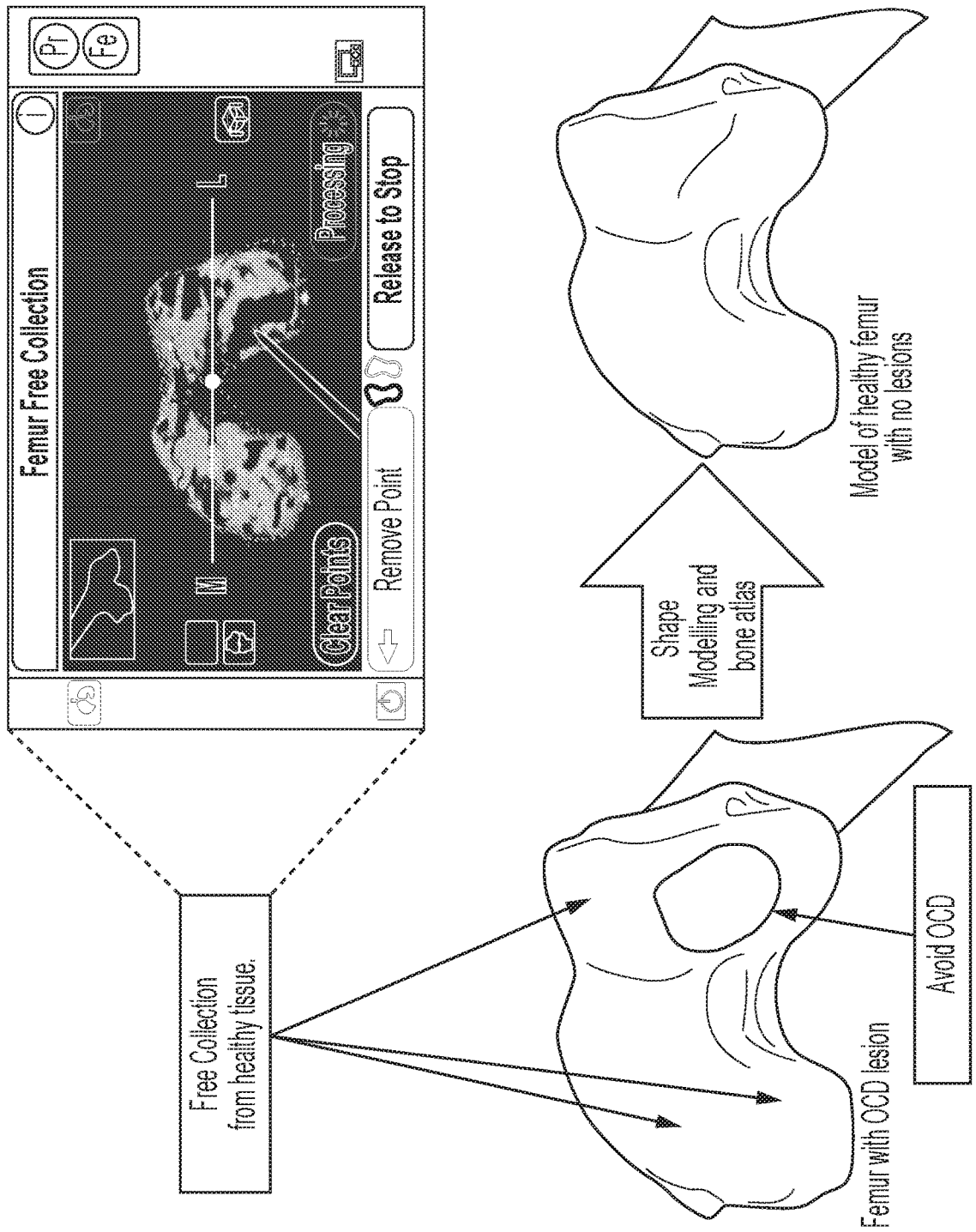
FIG. 6 depicts a flow diagram illustrating a method for generating a 3D healthy bone model in accordance with the embodiment of FIG. 5.

As illustrated in step 520, a 3D healthy bone model is generated using the mapped articular surface of the joint from step 515. As shown in the flow diagram of FIG. 6, in an embodiment, the articular surface point data and data from a database of healthy bone anatomies are applied to a statistical modeling equation to generate a 3D healthy bone model with no bone lesions. In an embodiment, generating the 3D healthy bone model is performed intraoperatively. In an embodiment, generating the 3D healthy bone model is performed preoperatively. This bone model can include an ideal osteochondral surface to target with the implant to correct the defect.

As illustrated in step 525, the instrumented probe is used to define the boundary of the defect onto the 3D healthy bone model generated in step 520. In an embodiment, the instrumented probe is used to define the boundary of the defect before the 3D healthy bone model is generated. In an embodiment, the instrumented probe may define the boundary of the OCD using Cartesian coordinates, spherical coordinates, cylindrical coordinates, or any other suitable coordinate system. In an embodiment, defining the OCD boundary is performed intraoperatively. In an embodiment, defining the OCD boundary is performed preoperatively. In an alternative embodiment, defining the boundary of the OCD defect 525 may be performed before generation of the 3D healthy bone model 520. In an alternative embodiment, defining the boundary of the OCD defect 525 may be performed concurrently with or before collecting articular surface point data of the joint 515.

As illustrated in step 530, a 3D model of an implant for treating an osteochondral defect of a joint is generated. In an embodiment, the cross-sectional shape of the implant is based on the defect boundary defined in step 525. In an embodiment, the shape of the articular surface of the implant is based on the portion of the mapped articular surface of the joint that is within the boundary of the OCD as determined in step 525. In an embodiment, the shape of the articular surface of the implant is based on the portion of the 3D healthy bone model that is within the boundary of the OCD as determined in step 525. In an embodiment, the articular surface may be flat. In an embodiment, the articular surface may be shaped to be one or more of convex, concave, and saddle-shaped. In an embodiment, the preoperative images may be obtained using at least one of an X-ray, computerized tomography, and magnetic resonance imaging. In an embodiment, the dimensions and desired properties of the implant can be determined based on one or more of (1) the shape of the articular surface of the implant described further herein, (2) the thickness of the articular cartilage surrounding the OCD determined based on preoperative images of the joint, and (3) the depth of the OCD determined based on the preoperative images of the joint. In an embodiment, a surgeon could determine the thickness of the implant intraoperatively. In such an embodiment, the surgeon may enter the determined thickness prior to generating the 3D implant model. In an embodiment, the instrumented probe may be used to determine the thickness of the cartilage at a non-articular portion of the knee using a Shore hardness test. In an alternate embodiment, the instrumented probe may be used to determine the thickness of the cartilage by detecting the location of the instrumented probe while touching the surface of the cartilage and then detecting the location of the probe while touching bone. In an embodiment, generating the 3D implant model is performed intraoperatively. In an embodiment, generating the 3D implant model is performed preoperatively.

As illustrated in step 535, an implant may be manufactured based on the 3D implant model generated in step 530. In some embodiments, the implant is selected from a plurality of available implant models having a variety of dimensions, shapes, or chondral surface intrinsic characteristics. In an embodiment, the implant may be manufactured using one or more additive techniques. Additive techniques may include, for example, bio-plotting, fused deposition modeling (FDM), selective laser sintering (SLS), and stereolithography (SLA). In an embodiment, the manufacturing system may use one or more machining techniques. Machining techniques may include, for example, 5-axis computer numerical control (CNC). In an embodiment, a standard blank implant may be manufactured using one or more additive techniques and then refined using one or more machining techniques based on the 3D implant model generated in step 530. In an embodiment, refining a standard implant based on the 3D implant model may be performed intraoperatively.

In an embodiment, manufacturing the implant based on the 3D implant model includes manufacturing an implant according to the 3D model using one or more additive techniques. In an embodiment, manufacturing the implant according to the 3D implant model using one or more additive techniques is performed intraoperatively. In an embodiment, manufacturing the implant according to the 3D implant model using one or more additive techniques is performed preoperatively. In an alternative embodiment, a standard implant is manufactured using one or more additive techniques and then shaped according to the 3D implant model using one or more machining techniques. In an embodiment, manufacturing the standard implant using one or more additive techniques is performed preoperatively. In an embodiment, manufacturing the standard implant using one or more additive techniques is performed intraoperatively. In an embodiment, shaping the standard implant according to the implant model is performed intraoperatively. In an embodiment, shaping the standard implant according to the 3D implant model is performed preoperatively.

In an embodiment, manufacturing the implant based on the 3D implant model includes separately manufacturing one or more of the first segment, the second segment, and the one or more additional segments, as described further herein, and assembling them. In an embodiment, manufacturing the implant based on the 3D implant model includes successively manufacturing one or more of the first segment, the second segment, and the one or more additional segments, as described further herein, using additive techniques. In an embodiment, one or more coatings may be applied to the implant using one or more additive techniques.

In an embodiment, manufacturing the implant further includes sterilizing the manufactured implant for implantation. Sterilizing includes, for example, steam sterilization, dry heat sterilization, chemical sterilization, radiation sterilization, or any other suitable method. Steam sterilization includes, for example, flash sterilization. Chemical sterilization includes, for example, ethylene oxide sterilization.

As illustrated in step 540, an implantation plan may be generated. In an embodiment, generating the implantation plan may include determining the size, shape, location, and orientation of a cavity on the joint with the OCD for receiving the implant. In an embodiment, generating the implantation plan may include orienting the 3D implant model relative to the 3D healthy bone model to determine the proper location and orientation of the cavity on the joint.

In an embodiment, generating the implantation plan may include determining the size and shape of the cavity on the joint for receiving the implant based on the 3D implant model.

As illustrated in step 545, the joint may be resected to create a cavity on the joint for receiving the implant according to the implantation plan. In an embodiment, the resection may be performed by a CASS 100 or other surgical system. In some embodiments, resection may be performed with the assistance of a robotic arm. In an embodiment, the cavity may be shaped based on the 3D implant model to receive the implant. In an embodiment, resecting the joint to form a cavity on the joint may include removing the OCD. In an embodiment, removing the OCD includes preventing the removal of excess tissue using control instructions provided to the robotic surgical system. In an embodiment, preventing the removal of excess tissue includes controlling at least one of a speed and depth of a burr of the surgical robot. In an embodiment, preventing the removal of excess tissue includes stopping the motion of a burr of a surgical robot when the burr reaches a boundary of the planned cavity.

In some embodiments, resection 545 is performed by a surgeon with the assistance of a CASS 100 or robotically assistive surgical system, such as the NAVIO system. For example, fiducial markers on the surgeon's tool can be observed via a robotic vision system, and the operation of the tool can be governed by a processor in accordance with the surgical plan, thereby preventing the resection cavity from being too large or deviating from the surgical plan. This ensures proper fit of the implant.

In an embodiment, the operations of manufacturing 535 the implant and one or more of generating 540 an implantation plan and resecting 545 the joint according to the implantation plan may be performed concurrently. The shape of the resection of patient material and cartilage is determined from the implantation plan. The three-dimensional cavity created by this resection should match the matching surfaces of the implant. Depending on the tools used, the shape can be a rounded recess or a square recess.

As illustrated in step 550, the implant may be placed into the resected cavity on the joint. In an embodiment, the implant may be press-fitted into the cavity. In an embodiment, an adhesive may be applied to the implant before the implant is placed into the cavity. In an embodiment, the adhesive may be a biocompatible adhesive. In an embodiment, the adhesive may be a collagen adhesive. In some embodiments, the implant can include a bone tissue interfacing surface that is designed to encourage interlocking bone tissue growth into the implant. For example, a bio-inert material, such as titanium or tantalum, can be manufactured into a porous matrix or have a coating to provide a substrate onto which bone adheres as it heals. One exemplary material for this bone tissue interfacing surface is CONCELOC porous titanium from Smith and Nephew. CONCELOC is a registered trademark of SMITH & NEPHEW, INC. of Memphis, TN. Other exemplary interfacing surface materials include tantalum or titanium alloys having a porous matrix or coating, such as those that trade under the marks TRABECULAR METAL, TRITANIUM, REGENEREX, STIKTITE, or GRIPTION. TRABECULAR METAL is a registered trademark of Zimmer Biomet of Warsaw, IN. TRITANIUM is a registered trademark of Stryker Corp. of Kalamazoo, MI. REGENEREX is a registered trademark of Zimmer Biomet of Warsaw, IN. STIKTITE is a registered trademark of SMITH & NEPHEW, INC. of Memphis, TN. GRIPTION is a registered trademark of DePuy Synthes of Warsaw, IN. In some embodiments, the insertion and securing of the implant can include insertion of one or more screws or pins to help secure the implant while bone grows into the implant.

In an embodiment, the implant may further include the injection of one or more materials around an outer surface of the implant or into a bone-mating surface of the implant to aid in adherence or bonding to resected bone and in regeneration of tissue to mechanically interlock the implant as the bone heals. In an embodiment, the material may be a fluid. In an embodiment, the type of cartilage may be a synthetic hyaline-like cartilage. In an embodiment, the fluid may include chondrocytes, moselized bone, blood platelet concentrate, bone marrow, stem cells, growth factors, extracellular matrix (ECM), or a combination thereof. In an embodiment, the fluid may stimulate growth of a type of bone. In an embodiment, the type of bone may be sub-chondral bone. In an embodiment, the type of bone may be cancellous bone. Stem cells may include progenitor cells, for example, embryonic stem cells, mesenchymal stem cells (MSCs) and adipose tissue-derived stem cells. Growth factors may include, for example, vascular endothelial growth factors (VEGF), insulin-like growth factors (IGF), transforming growth factors (TGF), fibroblast derived growth factors (FDGF), platelet derived growth factors (PDGF), and bone morphogenic protein (BMP). In an embodiment, the injection may be performed one or more of intraoperatively and postoperatively. In an alternative embodiment, the injection may be performed preoperatively.

Figure 7:
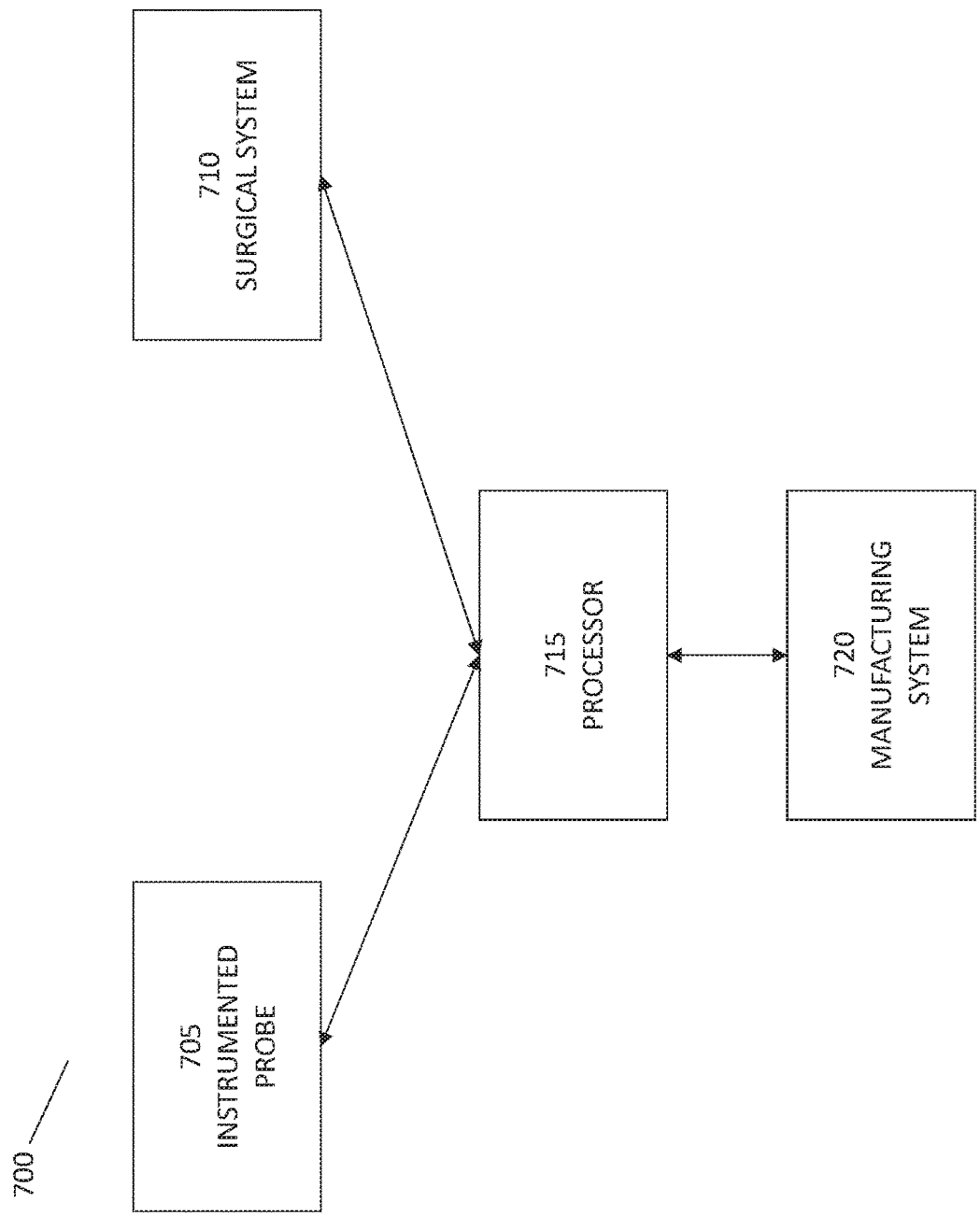
FIG. 7 depicts a block diagram of an image-free system for treatment of an OCD of a joint in accordance with an embodiment.

FIG. 7 depicts an operative patient care system and illustrative data sources in accordance with an embodiment. As shown in FIG. 7, the operative patient care system 700 may include an instrumented probe 705, a surgical system 710, a processor 715, and a manufacturing/selection system 720. In an embodiment, the manufacturing/selection system 720 uses one or more additive techniques to manufacture custom implants responsive to the processor 715 and the results obtained by the probe 705. In some embodiments, the manufacturing/selection system 720 recommends a prefabricated implant that suits the needs of the patient's particular OCD. The manufacturing techniques can include any discussed throughout. In an embodiment, the additive technique allows for the creation of interconnected porosity within a manufactured item. In an embodiment, the manufacturing system may use one or more machining techniques. Machining techniques may include, for example, 5-axis computer numerical control (CNC). In some embodiments, additive techniques are used, which can include, bio-plotting, fused deposition modeling (FDM), selective laser sintering (SLS), and stereolithography (SLA).

In some embodiments, a bio-inert material (e.g. titanium, stainless steel, or an alloy thereof) is used with these additive techniques to act as a rigid or semi-rigid substrate onto which simulated cartilage can be over-molded through an injection molding process. This may result in simulated cartilage that has desired intrinsic properties (e.g., compliance, absorbency, permeability, etc.) and extrinsic properties (e.g., dimensions and shape) and a substrate that can be affixed to the bone via adhesives or interconnection via bone growth. Traditionally, certain synthetic cartilage materials have been difficult to manufacture in a manner that provides sufficient adhesion to a metal base layer substrate or to bone. Embodiments address this issue by using a metal substrate that includes a porous layer to allow the simulated cartilage material to be injected into and mechanically interlock with the substrate during injection molding. Once the simulated cartilage material cures, this allows strong mechanical adhesion between the metal substrate and the molded simulated cartilage.

In some embodiments, the substrate onto which the synthetic cartilage is over-molded includes a layer constructed of CONCELOC or a similar material. CONCELOC is a titanium alloy (Ti-6Al-4V) constructed via laser or electron beam deposition to sinter metal powder on a layer-by-layer manner to create an interconnected network of random pores with a porosity of up to 80% near the surface. Generally, overall porosity is around 65% in some embodiments. Typical pore sizes range from 202 µm to 934 µm, in some embodiments, although other suitable ranges can be used to optimize adhesion to a synthetic cartilage or to bone. This provides a porous matrix into which synthetic cartilage can be injected during an over-molded injection molding process. In some embodiments, top and bottom layers of the substrate are constructed of a porous titanium alloy, such as CONCELOC, allowing injection molding of the synthetic cartilage on top and an exposed porous surface on the bottom that provides a matrix for interlocking with bone as it heals.

Figure 8:
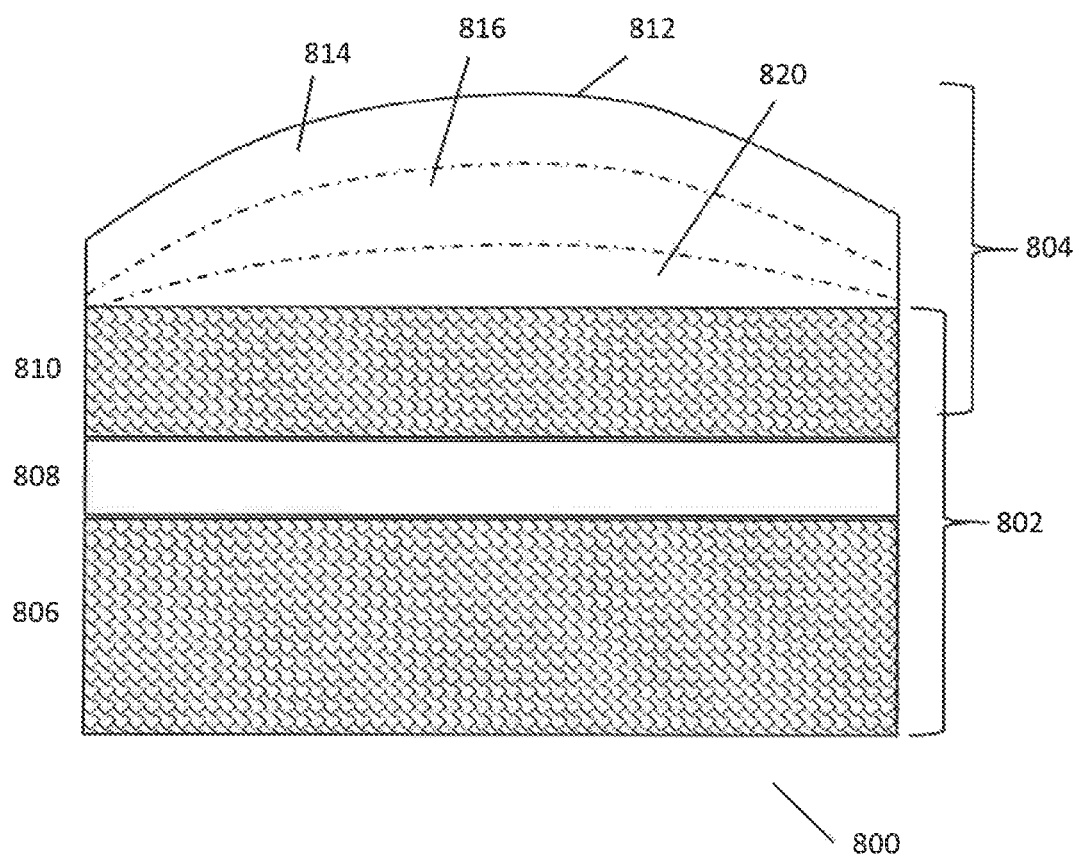
FIG. 8 depicts a cross-sectional view of an exemplary implant manufactured in accordance with some embodiments.

FIG. 8 is a cross-sectional diagram of an exemplary synthetic cartilage implant 800 for repairing an OCD (not necessarily to scale). There are two primary components to the implant 800: a substrate 802 and a synthetic cartilage material 804. In some embodiments, the substrate 802 is a 3-D printed (additive manufacturing) structure comprising a titanium alloy printed to include a first porous matrix 806, an intervening nonporous section 808 and a second porous matrix 810. In some embodiments, sections 806, 808, and 810 are all adequately manufactured using the same sintered material. The size of the pores for the first and second porous matrices 806 and 810 can be selected based on the materials for the interface. The first porous matrix 806 may interface with cortical or cancellous bone depending on the preoperative plan. As the bone heals, the bone structure grows into the interconnected pores of the first porous matrix 806 to create a mechanical interlocking structure to secure the implant 800 to the healing bone. The second porous matrix 810 provides a lattice substrate into which the synthetic cartilage polymer material 804 can be injected during an over-molding process. As the polymer material 804 cures, the polymer material is trapped in the interconnecting pores of the second porous matrix 810, which causes the polymer material to be mechanically interlocked to the substrate 802. The relative pore size and depth of matrices 806 and 810 can differ in accordance with the mechanical needs of the substrate 802. The intervening nonporous section 808 serves to provide a barrier between the porous matrices 806 and 810. More particularly, the intervening nonporous section 808 prevents the synthetic cartilage polymer material 804 from seeping into the first porous matrix 806, and ensures that the first porous matrix can be used entirely for bone growth. The exact dimensions of the substrate 802 are dictated by the pre-surgical plan and the extent of the OCD injury being repaired.

In an embodiment, the porous matrices 806 and 810 have interconnected porosity. In an embodiment, the porous matrices 806 and 810 have a polyhedral structure. In an embodiment, the polyhedral structure may be a combination of one or more lattice structures. The lattice structures may be, for example, cubic, diamond-shaped, tetrahedral, octahedral, or any other suitable structure. In an embodiment, the porous matrices 806 and 810 have a structure to mimic a type of bone. In an embodiment, the mimicked bone type may be sub-chondral bone. In an embodiment, the mimicked bone type may be cancellous bone. In an embodiment, the porous matrices 806 and 810 have pores having a diameter in the range of about 30-500 micrometers (µm). For example, the porous matrices 806 and 810 have pores having a diameter in the range of about 30-250 µm. In an embodiment, the porous matrices 806 and 810 have pores having a diameter in the range of about 30-150 µm. In an embodiment, the porous matrices 806 and 810 have pores having a diameter in the range of about 500-700 µm. In some embodiments, the porous matrices 806 and 810 have pores having a diameter in the range of about 202-934 µm. In various embodiments, the material chosen for the substrate 802 comprises one or more metals. Such metals may include, for example, porous titanium, titanium, titanium alloy, stainless steel, tantalum, or any other suitable material. In some embodiments, porous matrices 806 and 810 may have different porosity and pore sizes, each optimized to receiving bone growth and polymer materials, respectively.

The synthetic cartilage material 804 comprises one or more polymers that are over-molded via an injection molding process to interlock with pores in the second porous matrix 810 and secure the synthetic cartilage material to the substrate 802. In an embodiment, the synthetic cartilage material 804 comprises one or more synthetic organic polymers, one or more natural polymers, a copolymer of one or more thereof, or a blend of one or more thereof. In some embodiments, synthetic organic polymers may include, for example, porous polyurethane, polyurethane, acrylonitrile butadiene styrene (ABS), polylactic acid (PLA), polylactic-co-glycolic acid) (PLGA), poly(ε-caprolactone) (PCL), polyether ether ketone (PEEK), poly(ethylene glycol) (PEG), ultra-high molecular weight polyethylene (UHMWPE), polyether urethane or any other suitable material. Natural polymers include, for example, chitosan, collagen, gelatin, or any other suitable material.

In some embodiments, the synthetic cartilage material 804 comprises fully interpenetrating polymer networks (IPNs) and semi-interpenetrating polymer networks (semi-IPNs). IPNs and semi-IPNs can combine the beneficial properties of the polymers from which they are made and can avoid some of the undesirable properties of their component polymers. Exemplary IPNs utilize polymers, and may be hydrophobic polymers in some embodiments. The polymers may be thermoset, thermoplastic, linked, or cross-linked. By introducing a solvent, monomer, or another polymer to these polymers, new properties can be imparted. For example, lubriciousness can be introduced to a thermoplastic material by adding polymerizing ionic monomers/polymers. An otherwise hydrophobic polymer can be made to be hydrophilic, resulting in a low friction surface that mimics natural cartilage. By converting otherwise hydrophobic materials into biphasic materials with both solid and liquid (hydrated) phases, high strength and lubriciousness can be introduced to a single thermoplastic. An exemplary synthetic cartilage material 804 includes polyether urethane (PEU) that can be linked to a second polymer after molding. For example, acrylic acid, such as polyacrylic acid (PAA), can be added to cross-link with the PEU to cause the resulting IPN to be hydrophilic and swell in an aqueous solution. This allows the portion of the polymer that has been crosslinked to become lubricious, to create a surface of the strong or rigid polymer that has low friction when used as a synthetic cartilage. This allows for the creation of strong synthetic cartilage that has desirable surface qualities and surface compliance. Various suitable polymer materials for creation of these IPNs and semi-IPNs are discussed in detail in U.S. Pat. No. 8,883,915 to Myung, which is incorporated herein by reference. In an alternative embodiment, the synthetic cartilage material may be made from a polyglycolic acid (PGA). For example, the synthetic cartilage material may be a PGA/PGA gel available from Poly-Med, Inc. of Anderson, SC.

Polymer material 804 can be any thermoset or thermoplastic polymer that is suitable for an injection molding process and that can be cross-linked to a suitable polymer or monomer to create an IPN or semi-IPN having properties suitable for mimicking cartilage. In some embodiments, the polymer material 804 is a PEU material. To create a polymer material 804 having the desired shape that is bonded to the substrate 802, an over-molding injection molding process is used. A surface 812 of the polymer material 804 matches that of an injection mold. This injection mold can be created via a machining technique or an additive manufacturing process, such as 3-D printing. The exact shape of the surface 812 can be created using a standard mold or a mold that is customized to the patient anatomy based on a 3-D model of the desired cartilage shape. In some embodiments, the implant 800 is selected from a plurality of pre-manufactured implant designs, such that an implant having a surface 812 that most closely matches the ideal 3-D model is selected. In some embodiments, a custom mold is created for each patient, such that the surface 812 precisely approximates the ideal surface for implanting the 3-D model.

The over-molding process begins by setting the substrate 802 into a mold that includes sidewalls and a surface that matches the surface 812. This allows the substrate 802 to be over-molded. The resulting chamber created by the nonporous section 808, the walls of the mold, and the mold surface that matches the surface 812 is evacuated to remove air. A heated thermoplastic or thermoset polymer (or a polymer that can be cured from a liquid state) is injected under pressure into the evacuated chamber. This causes the liquid polymer to seep into the pores of the second porous matrix 810 under pressure. Thus, the interconnecting pores of second porous matrix 810 are generally filled with the liquid polymer. As the polymer material 804 cools/cures, the polymer creates a strong interconnecting bond with the second porous matrix 810. Once cooled/cured, the polymer material 804 and the substrate 802 are permanently fused, thereby creating a pseudo-monolithic structure.

Once the polymer material 804 is over-molded onto the substrate 802, the surface 812 is exposed to a suitable solvent, polymer, or monomer, such as PAA, to create an IPN or semi-IPN. The exact process by which the polymer/monomer and over-molded polymer are cross-linked can be any suitable process known in the art, such as those processes discussed in U.S. Pat. No. 8,883,915. This results in multiple layers within the polymer material 804. A surface layer 818, closest to the surface 812, may be thoroughly cross-linked, thereby creating an essentially heterogeneous IPN or semi-IPN. A second transition layer 816 may comprise a gradient of cross-linked polymer between a fully cross-linked IPN/semi-IPN and the original polymer material. A third layer 820 may comprise the original thermoplastic or thermoset polymer and have the same intrinsic qualities as that polymer. For example, the third layer 820 can be hydrophobic and rigid. In contrast, the surface layer 818 can be hydrophilic and compliant once hydrolyzed. The surface layer 818 can therefore act like a hydrogel with properties similar to cartilage. Meanwhile, the other two layers 816 and 820 may provide rigidity and transition between the lubricious absorptive surface layer 818 and the substrate 802. This creates a synthetic cartilage that is sturdy, but also compliant and lubricious to closely mimic properties of natural cartilage. Because the substrate 802 includes a first porous layer 806, this synthetic cartilage implant has a surface layer 818 and a surface 812 that mimic natural cartilage, while also fusing to patient bone as it heals.

Once manufactured, the implant 800 can be implanted into a resected bone cavity, and an aqueous solution can be applied to saturate and activate the surface layer 818 and the second transition layer 816. Alternatively, such layers 818 and 816 can be activated at the time of manufacture. Once implanted, the surgeon can maneuver the implant 800 such that the edges of the surface 812 are flush with surrounding cartilage. This can be achieved by planing portions of the surface layer 818 to remove any inconsistencies after implantation or by pressing or tapping the implant 800 with a tool that spans the gap between the existing cartilage and the edges of the surface 812.

Figure 9:
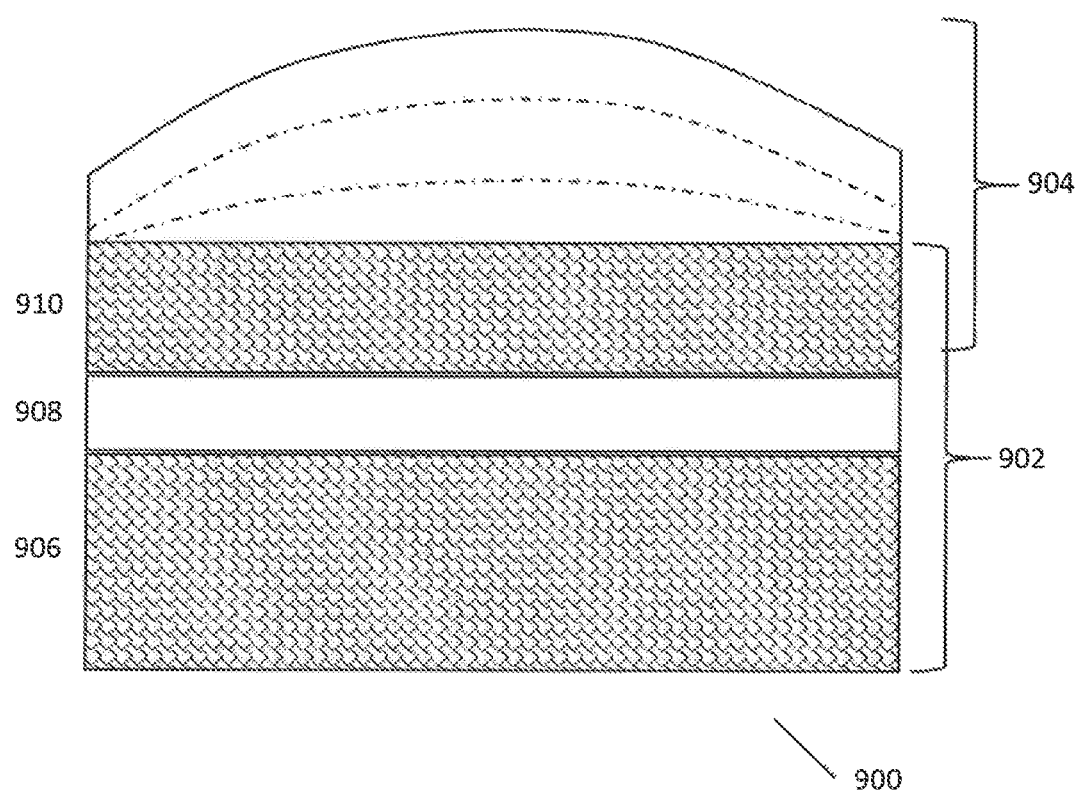
FIG. 9 depicts a side view of an exemplary synthetic cartilage implant in accordance with some embodiments.

FIG. 9 is a side view of an exemplary synthetic cartilage implant 900 for repairing an OCD (not necessarily to scale). There are two primary components to the implant 900: a substrate 902 and a synthetic cartilage material 904. In some embodiments, the substrate 902 is in the style of a screw-in or push-in bone anchor and includes a first portion 906, an intervening nonporous section 908 and a second portion 910. In some embodiments, sections 906, 908, and 910 are all adequately manufactured using the same material. The substrate 902 may be cannulated. The first portion 906 may interface with cortical or cancellous bone, depending on the preoperative plan. The first portion 906 may be threaded or have features, such as wings or ribs, that enable locking into bone after insertion. The first portion 906 may be shaped and of a material similar to that of a BIORAPTOR bone anchor or a HEALICOIL bone anchor. BIORAPTOR and HEALICOIL are registered trademarks of Smith & Nephew, Inc. of Memphis, TN. The second portion 910 provides a lattice substrate into which the synthetic cartilage polymer material 904 can be injected during an over-molding process. As the polymer material 904 cures, the polymer material is trapped in the interconnecting pores of the second portion 910, which causes the polymer material to be mechanically interlocked to the substrate 902. The intervening nonporous section 908 prevents the synthetic cartilage polymer material 904 from seeping into the first portion 906 and ensures that the first portion can be used entirely for bone growth. The exact dimensions of the substrate 902 are dictated by the pre-surgical plan and the extent of the OCD injury being repaired.

Figure 10:
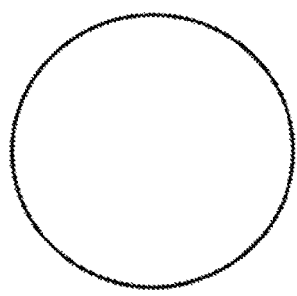
FIGS. 10-12 depict top view outlines of exemplary synthetic cartilage shapes in accordance with some embodiments.
Figure 11:
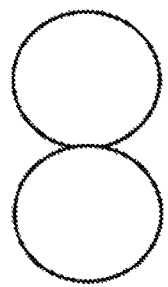
Figure 12:
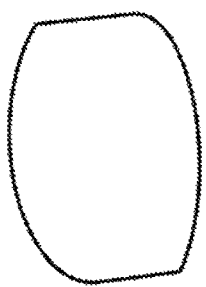

FIGS. 10-12 illustrate examples of synthetic cartilage implant shapes. In FIG. 10, the implant is generally a round cylinder. In FIG. 11, the implant is generally in the form of two or more overlapping cylinders. In FIG. 12, the implant has arcuate sides and straight ends. Those having ordinary skill in the art would understand that the implant can have any number of shapes or that the depicted shapes could be combined.

Treatment of full thickness, osteochondral focal lesions through either biological (OATS, ACI and microfracture) or porous synthetic implants can lead to pathological changes in the sub-chondral bone, such as thickening of the sub-chondral bone and formation of sub-chondral cysts and intralesional osteophytes. In particular, synovial fluid intrudes the bone when the bone attempts to heal by osteoclastic resorption of the necrotic bone creating fluid-filled spots that form in the sub-chondral bone. Cysts also are associated with increased cellular activity as well as increased numbers of macrophages and multinucleated cells. Pathologic fracture can occur at the site of a bone cyst given that the cyst can weaken the bone and destabilize the implant. An acellular or regenerative scaffold, which is designed to prevent the passage of the synovial fluid through the sub-chondral bone, could have potential clinical benefits in terms of reducing the risk of a fracture, which can destabilize the fixation of the implant.

Figure 13:
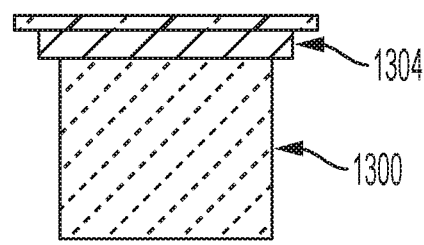
FIG. 13 depicts an illustrative implant having a tri-phasic scaffold design in accordance with some embodiments.
Figure 14:
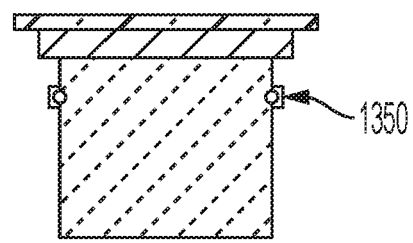
FIG. 14 depicts an alternate implant including a ring in accordance with some embodiments.
Figure 15:
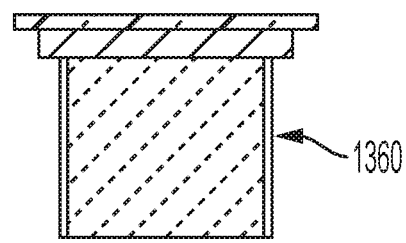
FIG. 15 depicts an alternate implant including barbs in accordance with some embodiments.

In other embodiments, the implant 1300 includes a triphasic scaffold design having a sub-chondral unit, a solid, impervious "intermediate" layer 1304 and a chondral layer, as shown in FIG. 13. The sub-chondral unit may be porous to allow bone infiltration and blood flow within the unit to ensure rapid fixation with the surrounding bone. The sub-chondral unit can be either a printed or woven structure and can be made from either a single or a combination of organic materials, e.g. Beta-tricalcium phosphate (β-TCP) and hydroxyapatite (HA), and inorganic materials, e.g. polyesters such as Polycaprolactone (PCL) or Poly (L-lactide-co-e-caprolactone) (PLC) copolymers. The osteochondral unit also can be functionalized with biomolecules, such as aggrecan and/or transforming growth factor beta 1 (TGF-β1), to help stimulate matrix formation and sequester progenitor cells. The sub-chondral unit also can have a graduated structure in order to match the physical and biochemical properties of the native tissue. The primary function of the impervious intermediate layer 1304 directly above the osteochondral unit is to prevent the ingress of synovial fluid, which is known to create sub-chondral bone cysts. The impervious intermediate layer 1304 is solid and non-porous, and can be created by altering the laser scanning parameters, which can create a natural transition between porous and solid structures. The impervious intermediate layer 1304 could be made from an inorganic material, an organic material, or a combination of these materials. A purely synthetic material used to make the impervious intermediate layer 1304 could be a degradable polymer, e.g. PLA, PGL, PCL, poly-tyrosine carbonates, polyurethanes, etc., and blends and/or co-polymers thereof. The impervious intermediate layer 1304 may be subjected to a post-chemical treatment to help repel the ingress of synovial fluid penetrating the sub-chondral bone. The chondral unit can be either a printed or woven structure that is attached to the intervening layer. The chondral unit can be solid, non-porous or porous with or without a graduated structure and optionally functionalized with biomolecules to help prevent the ingress of synovial fluid from the top surface. As best seen in FIG. 14, the geometrical structure of the chondral layer can be designed in such a way that it can be seated within a recess in the bone providing further protection to the sub-chondral bone directly beneath the scaffold. In the embodiment depicted in FIG. 14, a ring 1350 is included in the geometric structure. Alternatively or additionally, the edges of the chondral layer also could be angled to improve the level of interference between the chondral layer and the surrounding cartilage. For example, barbs 1360 are depicted in FIG. 15.

In other embodiments, the ingress of synovial fluid through the walls of the defect in the bone cavity may be prevented using an impervious bone adhesive, such as a fibrin sealant or other medical grade dental sealants. Such a bone adhesive may have hydrophobic properties.

In other embodiments, an impervious layer is created through a series of spot welds between the walls of the sub-chondral component of the scaffold and the neighboring bone cavity using an RF source. Creating an impervious layer using spot welds may be performed if the scaffold is constructed using a polymer with a low melting point, such as PCL.

In other embodiments, an adhesive liquid could be used to both join and seal the interface between the sub-chondral and chondral layers. For example, the sub-chondral component of the scaffold could be placed and covered with an adhesive. The cartilage component may be attached to the adhesive layer. In some embodiments, the adhesive may be a liquid, e.g., CaP cement, molten PCL, or molten degradable polymer. In some embodiments, the adhesive could be a pre-shaped layer, e.g. an adhesive sheet cut to shape, that is sandwiched between the two scaffold components in-situ. Additional and/or alternate adhesive layers and methods by which the adhesive is placed may be used within the scope of this disclosure.

In alternate embodiments, a degradable O-ring 1350 could be used to help seal the edges of the device. In such embodiments, the device may be made from a flexible material, such as poly-lactide or polycapraloctone polymer. The O-ring 1350 may provide a seal to prevent synovial fluid from penetrating around the edges of the implant 1300. In some embodiments, a surgical tool may be used to cut a groove into the sub-chondral bone to ensure that the O-ring 1350 remains flush with the surrounding tissue. The O-ring 1350 may provide additional stability and fixation of the implant 1300 in the sub-chondral bone.

In an alternate embodiment, an impervious intermediate layer 1304 may be created by attaching an impervious membrane (e.g., a periosteal patch) to a top surface of the scaffold. The impervious membrane may be either a synthetic polymer or a biological material, such as a collagen patch. The seal formed among the patch, the scaffold, and the surrounding tissue may be augmented by suture fixation or a suitable tissue sealant, such as cross-linked hyaluronic acid.

In yet another embodiment, a level of fixation between the sub-chondral unit and the surrounding bone may be further enhanced by using either a porous or solid sub-chondral anchor made from, for example and without limitation, bioceramics (HA, TCP) and/or degradable polymers (PCL, PLC).

Figure 16:
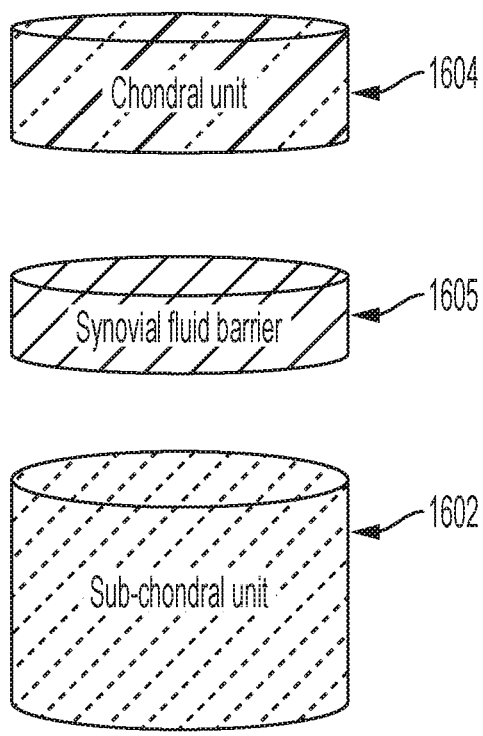
FIG. 16 depicts an exploded view of an illustrative implant in accordance with some embodiments.

As best seen in FIG. 16, an implant may include a sub-chondral unit 1602, a chondral unit 1604, and a synovial fluid barrier 1605. The chondral unit 1604 may be, for example and without limitation, printed or woven. The chondral unit 1604 may be either solid or porous. In some embodiments, the chondral unit 1604 may overhang the synovial fluid barrier 1605.

The synovial barrier 1605 may be, for example and without limitation, printed or woven. In some embodiments, the synovial barrier 1605 may have a gradient composition. In some embodiments, the synovial barrier 1605 may be bio-functionalized.

The sub-chondral unit 1602 may be, for example and without limitation, printed or woven. The sub-chondral unit 1602 may be either solid or porous. In some embodiments, the sub-chondral unit 1602 may be comprised of powder or microspheres.

Figure 17:
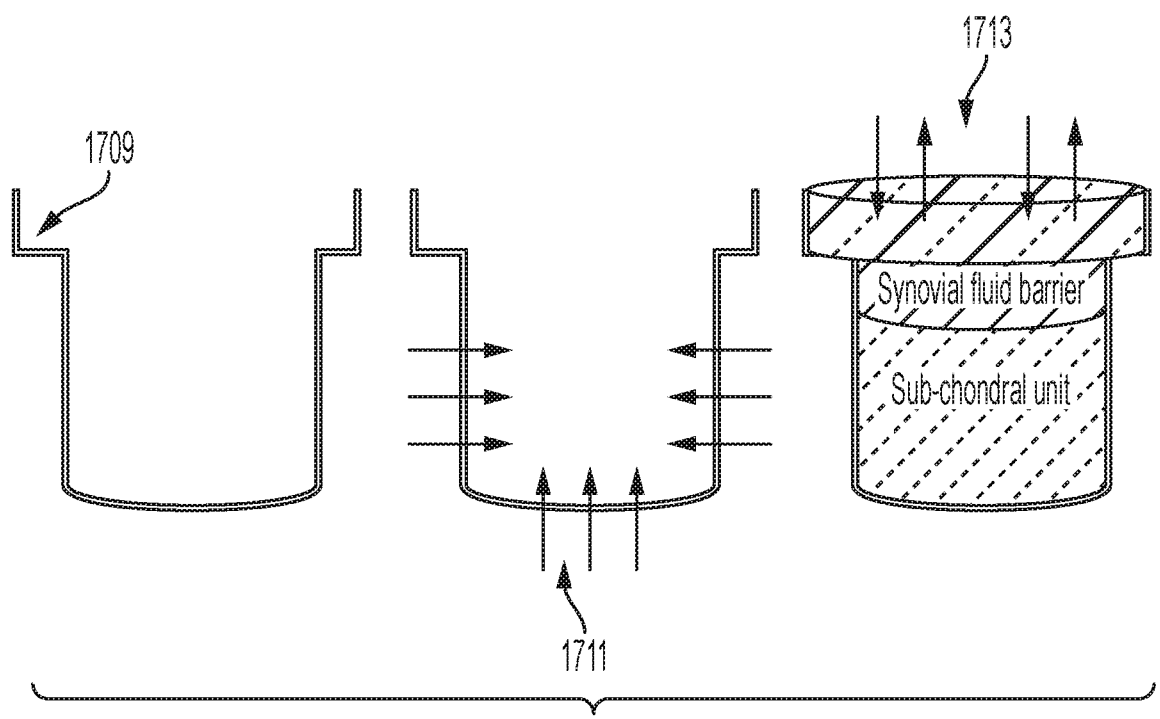
FIG. 17 depicts an illustrative implant including fluid flow within the implant post-insertion in accordance with some embodiments.

As best seen in FIG. 17, the defect may be prepared. In some embodiments, a shelf 1709 may be created at the site of the defect. In such embodiments, the shelf 1709 may be used to aid in sealing the chondral layer. The local blood supply may be stimulated at the site of the defect, such as by microfracture. The implant may be inserted into the defect. The chondral shelf and the impervious intermediate layer (i.e., the synovial fluid barrier) may work in concert to prevent the ingress of synovial fluid 1717 through the chondral layer into the sub-chondral bone beneath the site of the defect. The stimulation of the local blood supply at the site of the defect may stimulate blood flow through the walls of the internal cavities of the bone defect 1711 to assist with the integration of the sub-chondral unit of the implant with the surrounding tissues. In some embodiments, the shelf 1709 or recess may provide a structure to which an adhesive is applied to increase bonding between the implant and the site of the defect.

Figure 18:
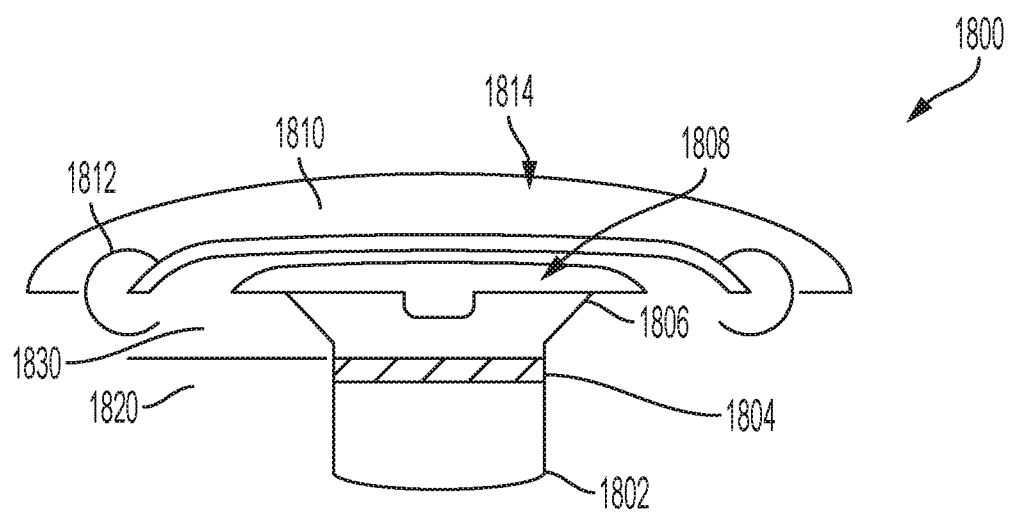
FIGS. 18-24 depict alternate implants in accordance with some embodiments.

Alternative embodiments for implants are depicted in FIGS. 18-24. As shown in FIG. 18, an implant 1800 may comprise a scaffold designed to be press fit into an osteochondral defect. The implant 1800 may include a porous sub-chondral portion 1802, a solid, impervious intermediate layer 1804, and a chondral portion 1806. The sub-chondral portion 1802 may be configured to be press fit into the sub-chondral bone 1820 through the cartilage 1830 at the site of the osteochondral defect. In an embodiment, the solid, impervious intermediate layer 1804 may be situated at or near the interface between the cartilage 1830 and the sub-chondral bone 1820. The chondral portion 1806 may extend through the cartilage 1830. In an embodiment, the chondral portion 1806 of the implant 1800 may be angled (with a screw-head-like appearance) in order to reduce the ingress of synovial fluid and increase the amount of pressure needed for synovial fluid ingress. A layer 1808 of hyaluronic acid or fibrin glue may be placed adjacent to a surface of the chondral portion 1806 that is exposed from the cartilage 1830. A periosteal flap 1810 may be placed distal from the cartilage 1830 and adjacent to the layer 1808 of hyaluronic acid or fibrin glue. The layer 1808 may cause the periosteal flap 1810 to adhere to the exposed surface of the chondral portion 1806 of the implant 1800. The periosteal flap 1810 may be connected to the cartilage 1830 using one or more sutures 1812 secured around the osteochondral defect to further secure the implant 1800 within the site of the defect. A second layer 1814 comprising fibrin glue may be applied over the periosteal flap 1810 and the sutures 1812 as another measure of sealing the osteochondral defect and preventing the ingress of synovial fluid into the osteochondral defect.

Figure 19:
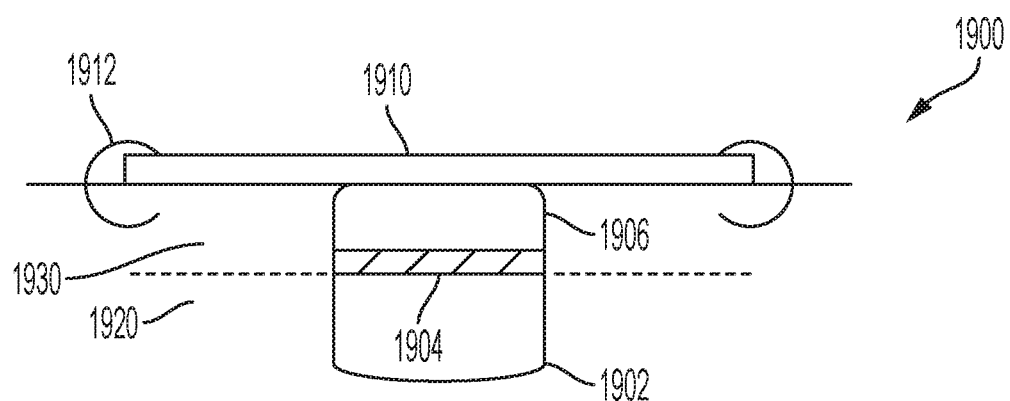

FIG. 19 depicts an alternate implant in accordance with some embodiments. As shown in FIG. 19, an implant 1900 may comprise a scaffold designed to be press fit into an osteochondral defect. The implant 1900 may include a porous sub-chondral portion 1902, a solid, impervious intermediate layer 1904, and a chondral portion 1906. The sub-chondral portion 1902 may be configured to be press fit into the sub-chondral bone 1920 through the cartilage 1930 at the site of the osteochondral defect. In an embodiment, the sub-chondral portion 1902 may comprise porous poly(ε-caprolactone) (PCL). In an embodiment, the solid, impervious intermediate layer 1904 may be situated at or near the interface between the cartilage 1930 and the sub-chondral bone 1920. In an embodiment, the impervious intermediate layer 1904 may comprise solid PCL. The chondral portion 1906 may extend through the cartilage 1930. A periosteal flap 1910 may be adhered to a surface of the chondral portion 1906 that is exposed from the cartilage 1930 with fibrin glue (not shown). The periosteal flap 1910 may be connected to the cartilage 1930 using one or more sutures 1912 secured around the osteochondral defect to further secure the implant 1900 within the site of the defect.

Figure 20:
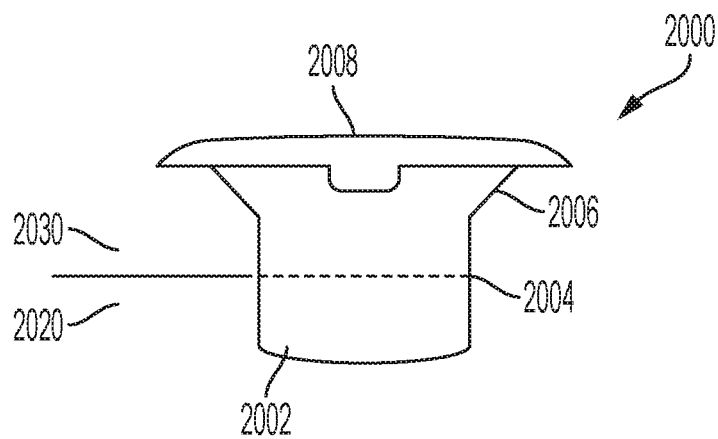

FIG. 20 depicts yet another alternate implant in accordance with some embodiments. As shown in FIG. 20, an implant 2000 may comprise a scaffold designed to be press fit into an osteochondral defect. The implant 2000 may include a porous sub-chondral portion 2002, a solid, impervious intermediate layer 2004, and a chondral portion 2006. The sub-chondral portion 2002 may be configured to be press fit into the sub-chondral bone 2020 through the cartilage 2030 at the site of the osteochondral defect. In an embodiment, the sub-chondral portion 2002 may comprise a 3D printed composition such as tricalcium phosphate (TCP) and/or porous PCL. In an embodiment, the solid, impervious intermediate layer 2004 may be situated at or near the interface between the cartilage 2030 and the sub-chondral bone 2020. The chondral portion 2006 may extend through the cartilage 2030. In an embodiment, the chondral portion 2006 may comprise transforming growth factor beta (TGF-β) tethered with a porous PCL. In an embodiment, the chondral portion 2006 may be 3D printed. In an embodiment, the chondral portion 2006 of the implant 2000 may be angled (with a screw-head-like appearance) in order to reduce the ingress of synovial fluid and increase the amount of pressure needed for synovial fluid ingress. A surface of the chondral portion 2006 that is exposed from the cartilage 2030 may be covered with a layer of methacrylated hyaluronic acid 2008. In an embodiment, the layer of methacrylated hyaluronic acid 2008 may be UV cross-linked in phase during implantation in order to prevent the ingress of synovial fluid into the osteochondral defect.

Figure 21:
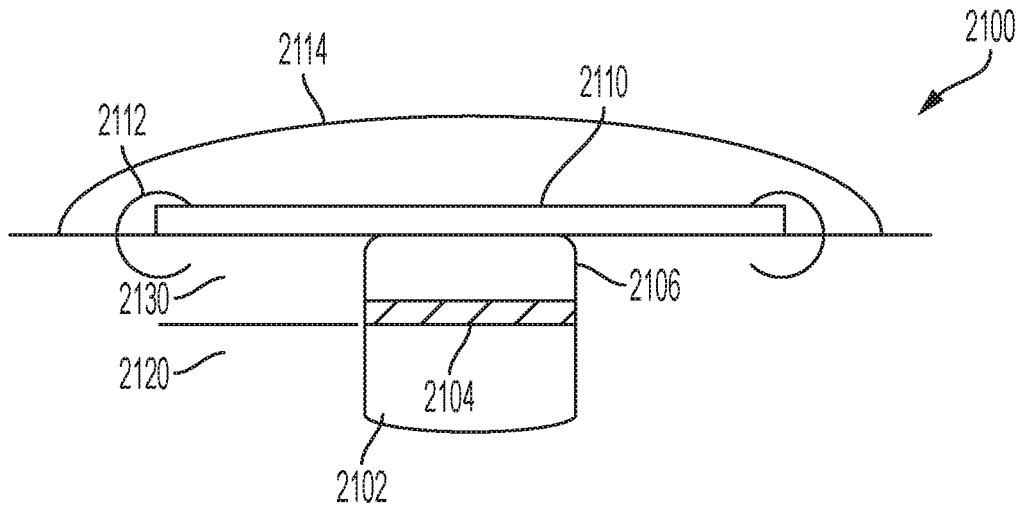

FIG. 21 depicts still another alternate implant in accordance with some embodiments. As shown in FIG. 21, an implant 2100 may comprise a scaffold designed to be press fit into an osteochondral defect. The implant 2100 may include a porous sub-chondral portion 2102, a solid, impervious intermediate layer 2104, and a chondral portion 2106. The sub-chondral portion 2102 may be configured to be press fit into the sub-chondral bone 2120 through the cartilage 2130 at the site of the osteochondral defect. In an embodiment, the solid, impervious intermediate layer 2104 may be situated at or near the interface between the cartilage 2130 and the sub-chondral bone 2120. In an embodiment, the solid, impervious intermediate layer 2104 may comprise hydroxyapatite and/or calcium phosphate. The chondral portion 2106 may extend through the cartilage 2130. A periosteal flap 2110 may cover a surface of the chondral portion 2106 that is exposed from the cartilage 2130. The periosteal flap 2110 may be connected to the cartilage 2130 using one or more sutures 2112 secured around the osteochondral defect to further secure the implant 2100 within the site of the defect. In an embodiment, a composition layer 2114 may cause the periosteal flap to adhere to the cartilage and/or the exposed surface of the chondral layer 2106 of the implant 2100. In some embodiments, the composition layer 2114 may comprise a UV cross-linked sealant, such as methacrylated hyaluronic acid or a type of dental resin polymer. In some embodiments, the composition layer 2114 may comprise fibrin glue.

Figure 22:
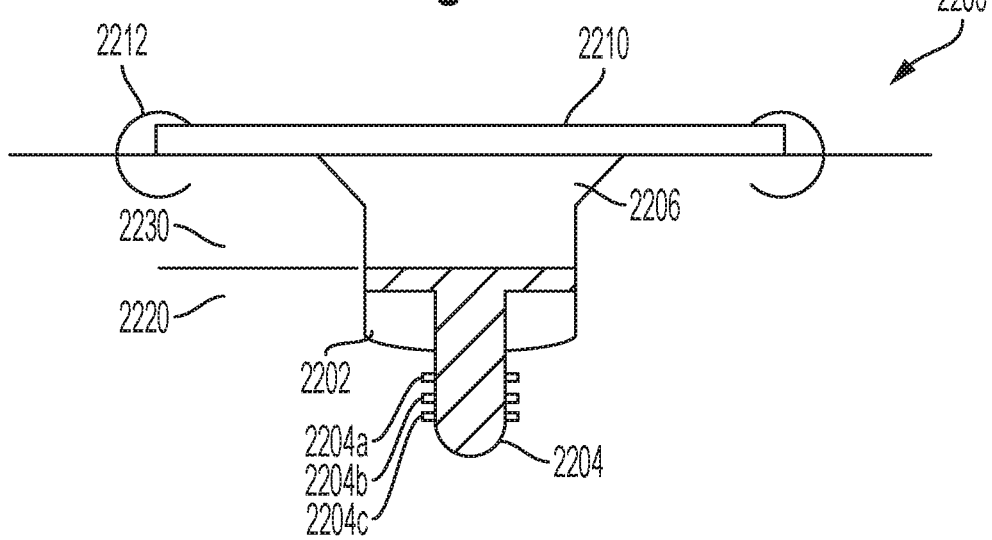

FIG. 22 depicts another alternate implant in accordance with some embodiments. As shown in FIG. 22, an implant 2200 may comprise a scaffold designed to be inserted into an osteochondral defect. The implant 2200 may include a porous sub-chondral portion 2202, an anchoring system 2204, and a chondral portion 2206. The sub-chondral portion 2202 may be configured to be inserted into the sub-chondral bone 2220 through the cartilage 2230 at the site of the osteochondral defect. In some embodiments, the implant scaffold may be slightly larger than the size of the osteochondral defect so that the implant 2200 may be press fit into the defect site. In an embodiment, the sub-chondral portion 2202 may comprise porous PCL. In an embodiment, a first end of the anchoring system 2204 may be situated at or near the interface between the cartilage 2230 and the sub-chondral bone 2220. The anchoring system 2204 may be configured to extend through and beyond the sub-chondral portion 2202 of the implant 2200. In some embodiments, the portion of the anchoring system 2204 extending beyond the sub-chondral portion 2202 may include one or more lateral extensions, such as 2204a-c, configured to more securely anchor the anchoring system within the sub-chondral bone. In an embodiment, the anchoring system may comprise solid PCL that is 3D printed around polycarbonate CaP. In some embodiments, the anchoring system 2204 may be inserted through the chondral portion 2206 of the implant 2200 intraoperatively by use of a surgical tool, such as a hammer. In some embodiments, the implant 2200 may be formed with the anchoring system 2204 in place and the implant may be inserted into the osteochondral defect and implanted by use of a surgical tool, such as a hammer. The chondral portion 2206 may extend through the cartilage 2230. In some embodiments, the chondral portion 2206 may comprise porous PCL. A periosteal flap 2210 may be adhered to a surface of the chondral portion 2206 that is exposed from the cartilage 2230 with fibrin glue (not shown). The periosteal flap 2210 may be connected to the cartilage 2230 using one or more sutures 2212 secured around the osteochondral defect to further secure the implant 2200 within the site of the defect.

Figure 23:
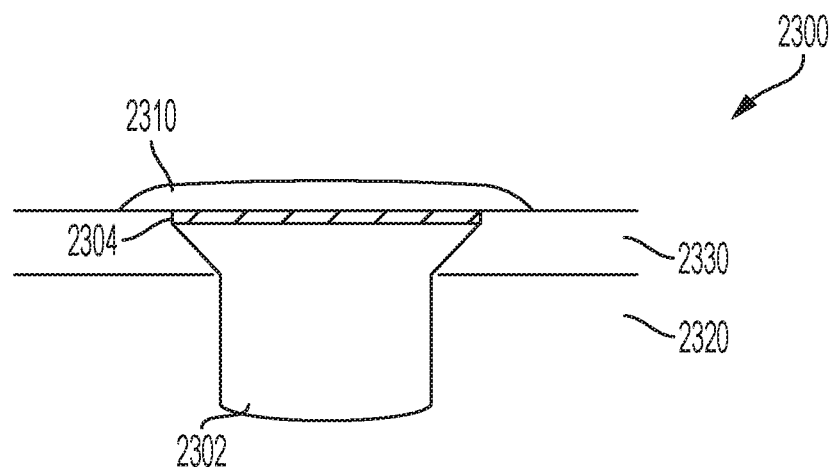

FIG. 23 depicts yet another alternate implant in accordance with some embodiments. As shown in FIG. 23, an implant 2300 may comprise a scaffold designed to be press fit into an osteochondral defect. The implant 2300 may include a porous portion 2302 and a solid, impervious portion 2304. The porous portion 2302 may be configured to be press fit into the sub-chondral bone 2320 through the cartilage 2330 at the site of the osteochondral defect. In an embodiment, the solid, impervious portion 2304 may be situated at or near the surface of the cartilage 2330. In an embodiment, the solid, impervious portion 2304 may comprise solid PCL. A periosteal flap and/or a composition layer 2310 may be used to cover a surface of the solid, impervious portion 2304. The periosteal flap 2310, if present, may be connected to the cartilage 2330 using one or more sutures (not shown) secured around the osteochondral defect to further secure the implant 2300 within the site of the defect. The composition layer 2310, if present, may comprise a UV cross-linked sealant, such as methacrylated hyaluronic acid or a type of dental resin polymer, or fibrin glue.

Figure 24:
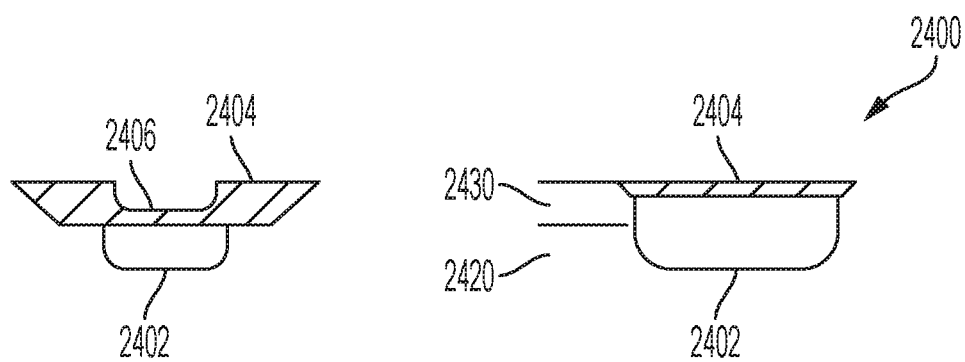

FIG. 24 depicts still another alternate implant in accordance with some embodiments. As shown in FIG. 24, an implant 2400 may comprise a scaffold designed to be press fit into an osteochondral defect. The implant 2400 may include a porous portion 2402 and a solid, impervious portion 2404. The porous portion 2402 may be configured to be press fit into the sub-chondral bone 2420 through the cartilage 2430 at the site of the osteochondral defect. In an embodiment, the solid, impervious portion 2404 may be situated at or near the surface of the cartilage 2430. In an embodiment, the solid, impervious portion 2404 may comprise solid PCL. In an embodiment, the solid, impervious layer 2404 may include a recess 2406 configured to receive an adhesive. In an embodiment, the solid, impervious layer 2404 may taper from a lesser diameter at the interface with the porous portion 2402 to a greater diameter at the surface of the implant 2400. This tapering of the solid, impervious layer 2404 may assist in deforming the cartilage 2430 for a tighter fit and may increase the amount of synovial fluid pressure required to penetrate the edges of the implant 2400.

Each of the implant scaffolds identified in FIGS. 18-21 and 23-24 may be slightly larger than the size of the osteochondral defect. As such, the implant may be press fit into the osteochondral defect as described above. In some methods, the scaffold may be soaked in blood from the creation of a bore hole within the defect prior to implantation. In some embodiments, a UV cross-linked sealant, such as methacrylated hyaluronic acid or type of dental resin polymer type, may be provided. In some embodiments, a periosteal flap with sutures along with fibrin glue or UV cross-linking polymer may be provided. In some embodiments, an anchoring system may be configured to secure the implant in a manner similar to a dry-wall anchor with a degradable polymer. In some embodiments, an anti-inflammatory regimen may be performed during implantation of the implant.

In some embodiments, a first portion of the synthetic cartilage implant includes a keel, a post, one or more wings, or any combination thereof. In some embodiments, one or more portions of the synthetic cartilage implant may include a hydroxyapatite coating. In some embodiments, one or more surfaces of the synthetic cartilage implant are roughened to promote cement adhesion.

While the implants and methods discussed herein have generally alluded to a small implantable plug that replaces a small OCD, it should be appreciated that these methods and implants could also be used for larger defects, such as partial or total knee or hip arthroplasty. In addition, although the implants described above in reference to FIGS. 18-24 incorporate particular features, it should be apparent to those of ordinary skill in the art that one or more features of a particular implant described above may be combined with one or more features of a second implant described above. In addition, one or more features disclosed in a particular embodiment in FIGS. 18-24 may be excluded from a particular implant and such implant would still be within the scope of this disclosure.

For purposes of this application, an "interpenetrating polymer network" or "IPN" is a material comprising two or more polymer networks which are at least partially interlaced on a molecular scale, but not covalently bonded to each other, and cannot be separated unless chemical bonds are broken. A "semi-interpenetrating polymer network" or "semi-IPN" is a material comprising one or more polymer networks and one or more linear or branched polymers characterized by the penetration on a molecular scale of at least one of the networks by at least some of the linear or branched macromolecules. As distinguished from an IPN, a semi-IPN is a polymer blend in which at least one of the component polymer networks is not chemically crosslinked by covalent bonds.

A "polymer" is a substance comprising macromolecules, including homopolymers (a polymer derived one species of monomer) and copolymers (a polymer derived from more than one species of monomer). A "hydrophobic polymer" is a pre-formed polymer network having at least one of the following two properties: (1) a surface water contact angle of at least 45° and (2) exhibits water absorption of 2.5% or less after 24 hours at room temperature according to ASTM test standard D570. A "hydrophilic polymer" is a polymer network having a surface water contact angle less than 45° and exhibits water absorption of more than 2.5% after 24 hours at room temperature according to ASTM test standard D570. An "ionic polymer" is defined as a polymer comprised of macromolecules containing at least 2% by weight ionic or ionizable monomers (or both), irrespective of their nature and location. An "ionizable monomer" is a small molecule that can be chemically bonded to other monomers to form a polymer and which also has the ability to become negatively charged due the presence of acid functional groups such carboxylic acid and/or sulfonic acid. A "thermoset polymer" is one that doesn't melt when heated, unlike a thermoplastic polymer. Thermoset polymers "set" into a given shape when first made and afterwards do not flow or melt, but rather decompose upon heating and are often highly crosslinked and/or covalently crosslinked. A "thermoplastic polymer" is one which melts or flows when heated, unlike thermoset polymers. Thermoplastic polymers are usually not covalently crosslinked. "Phase separation" is defined as the conversion of a single-phase system into a multi-phase system; especially the separation of two immiscible blocks of a block co-polymer into two phases, with the possibility of a small interphase in which a small degree of mixing occurs. Some embodiments modify common commercially available hydrophobic thermoset or thermoplastic polymers, such as polyurethane or ABS to provide suitable properties, such as strength, lubricity, electrical conductivity and wear-resistance. Other possible hydrophobic thermoset or thermoplastic polymers are described below. Embodiments can include IPN and semi-IPN compositions, as well as articles made from such compositions and methods of using such articles. The IPN and semi-IPN compositions may attain one or more of the following characteristics: High tensile and compressive strength; low coefficient of friction; high water content and swellability; high permeability; biocompatibility; and biostability.

As disclosed herein, a method, system, or device for treating an OCD may provide a treatment solution that is optimized for the particular OCD of a particular patient and may increase the likelihood that mobility will be restored to the joint because an implant model is generated for each OCD of each patient.

In addition, the teachings of the present disclosure may increase the likelihood of restoration of the weight bearing properties of the joint bearing the OCD because of the use of the database of healthy bone anatomies to generate a 3D healthy bone model restores the normal contours of the bone that may have been destroyed by the OCD.

Moreover, the teachings of the present disclosure may increase the likelihood of cartilage and/or bone growth because of the distinct optimized structures of the segments of the implant, the ability to inject biologic enhancements into the segments of the implant for targeted tissue growth, and the channels of the implant that are configured to facilitate blood flow into one or more segments of the implant.

Furthermore, the teachings of the present disclosure may increase the likelihood of restoration of the native articular surface because of the distinct segments of the implant that localize cartilage growth to one segment of the implant and bone growth to a second segment of the implant.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for correcting an osteochondral defect, the system comprising:
    a tracking system comprising:
        a probe having one or more probe tracking arrays, and
        one or more patient tracking arrays attached to a joint of a patient, wherein the tracking system is configured to detect a plurality of locations of the one or more probe tracking arrays and the one or more patient tracking arrays;
    one or more processors; and
    a non-transitory, computer-readable medium storing instructions that, when executed, cause the one or more processors to:
        receive the plurality of locations from the tracking system;
        generate, based on the plurality of locations, surface data related to an articular surface of a bone of the joint;
        define, based on the surface data, an outer boundary enclosing the osteochondral defect to designate a defect surface;
        generate, based on at least the surface data, a 3D healthy bone model that does not include the osteochondral defect;
        generate, based on at least the 3D healthy bone model and the outer boundary, a 3D implant model corresponding to the defect surface; and
        output the 3D implant model to a secondary device.

2. The system of claim 1, wherein the instructions, when executed, further cause the one or more processors to:
    receive library data from a library of healthy bone anatomies; and
    apply the surface data and the library data to a statistical modeling equation to generate the 3D healthy bone model.

3. The system of claim 1, wherein a shape of an articular surface of the 3D implant model is based on at least a portion of the 3D healthy bone model corresponding to the defect surface.

4. The system of claim 3, wherein the shape of the articular surface of the 3D implant model is further based on at least a portion of the surface data corresponding to the defect surface.

5. The system of claim 3, wherein the shape of the articular surface of the 3D implant model is further based on at least a thickness of articular cartilage of the joint.

6. The system of claim 1, wherein the secondary device comprises one or more of an implant manufacturing unit, a remote computer, a remote database, and a computer-readable data storage device.

7. The system of claim 1, wherein the 3D implant model comprises:
    a first porous layer configured for bone ingrowth;
    a non-porous layer joined to the first porous layer;
    a second porous layer joined to the non-porous layer opposite the first porous layer; and
    a cartilage material interlocked within pores in the second porous layer.

8. The system of claim 7, wherein:
    the first porous layer, the non-porous layer, and the second porous layer each comprise one or more of titanium, tantalum, and stainless steel; and
    the cartilage material comprises an interpenetrating polymer network including one or more of porous polyurethane, polyurethane, acrylonitrile butadiene styrene (ABS), polylactic acid (PLA), polylactic-co-glycolic acid) (PLGA), poly(ε-caprolactone) (PCL), polyether ether ketone (PEEK), poly(ethylene glycol) (PEG), ultra-high molecular weight polyethylene (UHMWPE), polyether urethane, chitosan, collagen, gelatin, polyacrylic acid (PAA), and polyglycolic acid (PGA).

9. The system of claim 1, wherein the instructions, when executed, further cause the one or more processors to:
    generate, based on the 3D healthy bone model and the 3D implant model, an implantation plan comprising one or more characteristics of a cavity on the bone for receiving the implant.

10. The system of claim 9, further comprising a surgical system having a robotic arm configured to resect the bone to form the cavity based on the implantation plan.

11. A method of correcting an osteochondral defect comprising:

generating, by a processor, surface data related to an articular surface of a bone of a joint, the articular surface comprising the osteochondral defect, wherein the surface data is based on a plurality of locations of a tracked probe;

defining, using the tracked probe, an outer boundary enclosing the osteochondral defect to designate a defect surface;

generating, based on at least the surface data, a 3D healthy bone model that does not include the osteochondral defect;

generating, based on at least the 3D healthy bone model and the outer boundary, a 3D implant model corresponding to the defect surface; and outputting the 3D implant model to a secondary device.

12. The method of claim 11, wherein generating the 3D healthy bone model is further based on library data from a library of healthy bone anatomies, and wherein generating the 3D healthy bone model comprises applying the surface data and the library data to a statistical modeling equation.

13. The method of claim 11, wherein a shape of an articular surface of the 3D implant model is based on at least a portion of the 3D healthy bone model corresponding to the defect surface.

14. The method of claim 13, wherein the shape of the articular surface of the 3D implant model is further based on at least a portion of the surface data corresponding to the defect surface.

15. The method of claim 13, wherein the shape of the articular surface of the 3D implant model is further based on at least a thickness of articular cartilage of the joint.

16. The method of claim 11, wherein the secondary device comprises one or more of an implant manufacturing unit, a remote computer, a remote database, and a computer-readable data storage device.

17. The method of claim 11, wherein the 3D implant model comprises:

a first porous layer configured for bone ingrowth;

a non-porous layer joined to the first porous layer;

a second porous layer joined to the non-porous layer opposite the first porous layer; and a cartilage material interlocking within pores in the second porous layer.

18. The method of claim 17, wherein:

the first porous layer, the non-porous layer, and the second porous layer each comprise one or more of titanium, tantalum, and stainless steel; and the cartilage material comprises an interpenetrating polymer network including one or more of porous polyurethane, polyurethane, acrylonitrile butadiene styrene (ABS), polylactic acid (PLA), polylactic-co-glycolic acid (PLGA), poly($\varepsilon$-caprolactone) (PCL), polyether ether ketone (PEEK), poly(ethylene glycol) (PEG), ultra-high molecular weight polyethylene (UHMWPE), polyether urethane, chitosan, collagen, gelatin, polyacrylic acid (PAA), and polyglycolic acid (PGA).

19. The method of claim 11, further comprising:

manufacturing an implant based on the 3D model;

generating, based on the 3D healthy bone model and the 3D implant model, an implantation plan comprising one or more characteristics of a cavity on the bone for receiving the implant;

resecting the bone to form the cavity based on the implantation plan; and inserting the implant into the cavity based on the implantation plan.

20. The method of claim 19, further comprising injecting a fluid material around an outer surface of the implant, wherein the fluid material comprises one or more of chondrocytes, morselized bone, blood platelet concentrate, bone marrow, stem cells, growth factors, and extracellular matrix.

* * * * *